United States Patent
Barker

(10) Patent No.: US 8,355,787 B2
(45) Date of Patent: *Jan. 15, 2013

(54) HIGH-RESOLUTION CONNECTOR FOR A NEUROSTIMULATION LEAD

(75) Inventor: John M. Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,934

(22) Filed: Sep. 23, 2011

(65) Prior Publication Data

US 2012/0016452 A1 Jan. 19, 2012

Related U.S. Application Data

(63) Continuation of application No. 12/423,721, filed on Apr. 14, 2009, now Pat. No. 8,046,074.

(60) Provisional application No. 61/046,675, filed on Apr. 21, 2008.

(51) Int. Cl.
*A61N 1/00* (2006.01)

(52) U.S. Cl. .......... 607/37; 607/116; 607/117; 607/118; 607/119; 607/122; 607/38; 439/909

(58) Field of Classification Search .............. 607/37, 607/116–119, 122; 439/909
See application file for complete search history.

(56) References Cited

U.S. PATENT DOCUMENTS

| | | | |
|---|---|---|---|
| 3,222,471 A | 12/1965 | Steinkamp | |
| 4,850,359 A | 7/1989 | Putz | |
| 4,869,255 A | 9/1989 | Putz | |
| 5,000,177 A | 3/1991 | Hoffman et al. | |
| 5,007,435 A | 4/1991 | Doan et al. | |
| 5,082,453 A | 1/1992 | Stutz, Jr. | |
| 5,241,957 A | 9/1993 | Camps et al. | |
| 5,348,481 A | 9/1994 | Ortiz | |
| 5,354,326 A | 10/1994 | Comben et al. | |
| 5,560,358 A | 10/1996 | Arnold et al. | |
| 5,782,892 A | 7/1998 | Castle et al. | |
| 5,843,141 A | 12/1998 | Bischoff et al. | |
| 5,989,077 A | 11/1999 | Mast et al. | |
| 6,038,479 A | 3/2000 | Werner et al. | |

(Continued)

OTHER PUBLICATIONS

PCT Communication Relating to the Results of the Partial International Search / Invitation to Pay Additional Fees for PCT/US2009/040563, Applicant: Boston Scientific Neuromodulation Corporation, Form PCT/ISA/206, dated Jul. 24, 2009 (4 pages).

(Continued)

*Primary Examiner* — Niketa Patel
*Assistant Examiner* — William Levicky
(74) *Attorney, Agent, or Firm* — Vista IP Law Group LLP

(57) ABSTRACT

An implantable connector comprises an electrically insulative housing including an outer wall, an interior cavity surrounded by the outer wall, a port through which the lead body portion can be introduced into the interior cavity, and a pair of first apertures disposed through the outer wall on a first side of the housing. The connector further comprises an electrical spring clip contact mounted to the housing. The contact includes a common portion and a pair of legs extending from opposite ends of the common portion. The legs respectively extend through the first apertures into the interior cavity, such that the legs firmly engage the electrical terminal therebetween when the lead body portion is introduced into the interior cavity.

18 Claims, 25 Drawing Sheets

U.S. PATENT DOCUMENTS

| | | | |
|---|---|---|---|
| 6,112,120 A | 8/2000 | Correas | |
| 6,154,678 A | 11/2000 | Lauro | |
| 6,162,101 A | 12/2000 | Fischer et al. | |
| 6,319,021 B1 * | 11/2001 | Billman | 439/78 |
| 6,343,233 B1 | 1/2002 | Werner et al. | |
| 6,397,108 B1 | 5/2002 | Camps et al. | |
| 6,415,168 B1 | 7/2002 | Putz | |
| 6,428,336 B1 | 8/2002 | Akerfeldt | |
| 6,430,442 B1 | 8/2002 | Peters et al. | |
| 6,662,035 B2 | 12/2003 | Sochor | |
| 6,671,534 B2 | 12/2003 | Putz | |
| 6,725,096 B2 | 4/2004 | Chinn et al. | |
| 6,741,892 B1 | 5/2004 | Meadows et al. | |
| 6,878,013 B1 | 4/2005 | Behan | |
| 6,895,276 B2 | 5/2005 | Kast et al. | |
| 6,913,478 B2 | 7/2005 | Lamrey | |
| 6,980,863 B2 | 12/2005 | van Venrooj et al. | |
| 7,058,452 B2 | 6/2006 | Dahberg | |
| 7,070,455 B2 | 7/2006 | Balsells | |
| 7,110,827 B2 | 9/2006 | Sage et al. | |
| 7,195,523 B2 | 3/2007 | Naviaux | |
| 7,244,150 B1 | 7/2007 | Brase et al. | |
| 7,650,184 B2 | 1/2010 | Walter | |
| 7,798,864 B2 * | 9/2010 | Barker et al. | 439/668 |
| 8,046,074 B2 * | 10/2011 | Barker | 607/37 |
| 2002/0143376 A1 | 10/2002 | Chinn et al. | |
| 2003/0163171 A1 | 8/2003 | Kast et al. | |
| 2004/0230268 A1 * | 11/2004 | Huff et al. | 607/116 |
| 2005/0027326 A1 * | 2/2005 | Ries et al. | 607/37 |
| 2005/0027327 A1 | 2/2005 | Ries et al. | |
| 2006/0224208 A1 | 10/2006 | Naviaux | |
| 2007/0042648 A1 | 2/2007 | Balsells | |
| 2007/0150036 A1 | 6/2007 | Anderson | |
| 2007/0161294 A1 | 7/2007 | Brase et al. | |
| 2007/0168004 A1 | 7/2007 | Walter | |
| 2007/0168007 A1 | 7/2007 | Kuzma et al. | |

OTHER PUBLICATIONS

PCT International Search Report for PCT/US2009/040563, Applicant: Boston Scientific Neuromodulation Corporation, Form PCT/ISA/210 and 220, dated Dec. 4, 2009 (8 pages).

PCT Written Opinion of the International Search Authority for PCT/US2009/040563, Applicant: Boston Scientific Neuromodulation Corporation, Form PCT/ISA/237, dated Dec. 14, 2009 (8 pages).

PCT International Preliminary Report on Patentability (Chapter I of the Patent Cooperation Treaty) for PCT/US2009/040563, Applicant: Boston Scientific Neuromodulation Corporation, Form PCT/IB/326 and 373, dated Nov. 4, 2010 (10 pages).

* cited by examiner

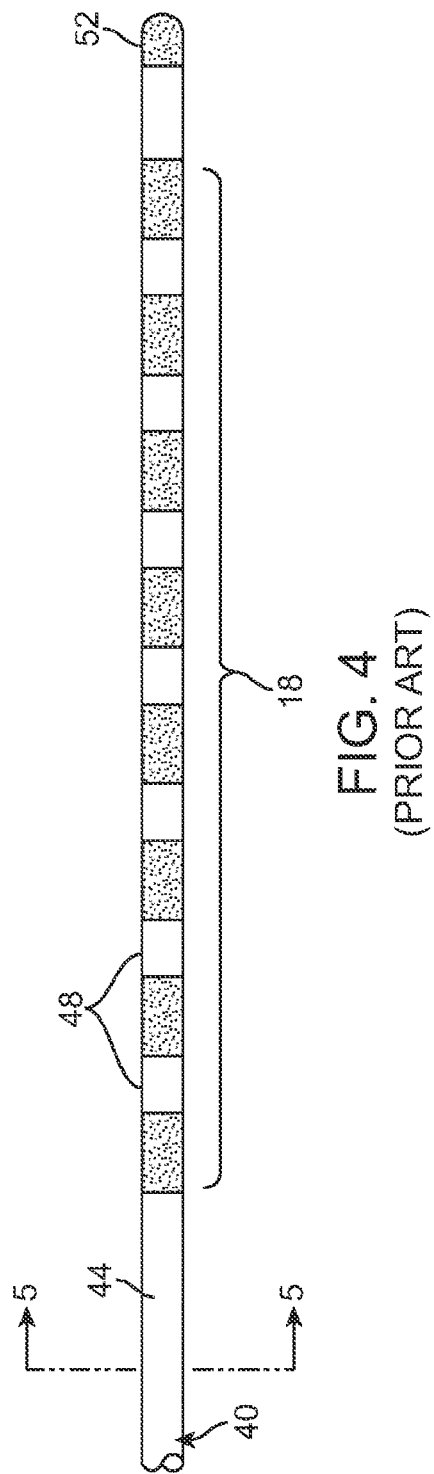
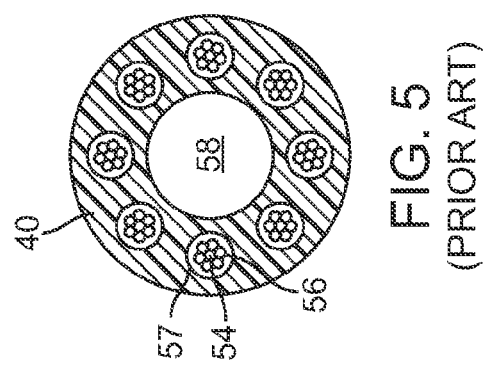
FIG. 4
(PRIOR ART)
FIG. 5
(PRIOR ART)

HIGH-RESOLUTION CONNECTOR FOR A NEUROSTIMULATION LEAD

RELATED APPLICATION

The present application is a continuation of U.S. patent application Ser. No. 12/423,721, filed Apr. 14, 2009, now issued as U.S. Pat. No. 8,046,074 which application claims the benefit under 35 U.S.C. §119 to U.S. provisional patent application Ser. No. 61/046,675, filed Apr. 21, 2008. The foregoing applications are hereby incorporated by reference into the present application in its entirety.

FIELD OF THE INVENTION

The present invention relates to tissue stimulation systems, and more particularly, to connectors for coupling neurostimulation leads to implantable neurostimulators, extension leads, and adapters.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more stimulation leads implanted at the desired stimulation site. In the context of an SCS procedure, one or more stimulation leads are introduced through the patient's back into the epidural space under fluoroscopy, such that the electrodes carried by the leads are arranged in a desired pattern and spacing to create an electrode array.

The specific procedure used to implant the stimulation leads in an SCS procedure will ultimately depend on the type of stimulation leads used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. In many cases, a stylet, such as a metallic wire, is inserted into a lumen running through the center of each of the percutaneous leads to aid in insertion of the lead through the needle and into the epidural space. The stylet gives the lead rigidity during positioning, and once the lead is positioned, the stylet can be removed after which the lead becomes flaccid.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

Each of the above-mentioned implantable neurostimulation systems also comprises an implantable neurostimulator, such as an implantable pulse generator (IPG), implanted remotely from the stimulation site, but coupled to the stimulation leads. Thus, electrical pulses can be delivered from the neurostimulator to the stimulation leads to stimulate the tissue and provide the desired efficacious therapy to the patient. In the context of an SCS procedure, the electrical pulses are delivered to the dorsal column and dorsal root fibers within the spinal cord. The stimulation creates the sensation known as paresthesia, which can be characterized as an alternative sensation that replaces the pain signals sensed by the patient.

Each stimulation lead may be directly coupled to the neurostimulator or indirectly coupled to the neurostimulator via an extension leads in cases where the length of the stimulation leads is insufficient to reach the neurostimulator.

If the stimulation leads are to be directly connected to the neurostimulator, the proximal ends of the stimulation leads can be inserted into a connector of the neurostimulator (via connector ports located on a header of the neurostimulator), such that the terminals located at the proximal ends of the stimulation leads are coupled to corresponding electrical contacts within the connector. Individual wires are routed though lumens in each stimulation lead to connect the proximally-located terminals with the distally-located electrodes.

If the stimulation leads are to be indirectly connected to the neurostimulator via the extension leads, the proximal ends of the stimulation leads can be inserted into connectors located at the distal ends of the respective extension leads, such that the terminals of the stimulation leads are coupled to corresponding electrical contacts within the connectors of the extension leads. The proximal ends of the extension leads can then be inserted into the connector of the neurostimulator, such that terminals located at the proximal ends of the extension leads are coupled to the corresponding electrical contacts within the connector of the neurostimulator. Individual wires are routed though lumens in each extension lead to respectively couple the proximally-located terminals to the distally-located electrical contacts.

After the system is fully implanted, it is important that the subcutaneously implanted components, such as the neurostimulator and extension leads, be of a low-profile nature for aesthetic reasons as well as to prevent or minimize any discomfort of the patient that may otherwise occur by having rigid objects that do not conform to the natural curvature and movement of the patient.

However, in order to accommodate the present-day contacts, which either take the form of metal collars containing set screws or Bal-Seal® contacts composed of springs contained within steel ring housings, the connectors of the extension lead and adapter are typically larger and stiffer than the bodies of the extension lead and adapter, thereby increasing the overall profile, while decreasing the conformity, of the extension lead and adapter. In addition, Bal-Seal® contacts are also relatively expensive, which given the number of contacts required, may result in a connector that is prohibitively expensive. Furthermore, metal collars for accommodating screws and the spring coil within the Bal-Seal® contacts are relatively long, thereby limiting the number of contacts that can be incorporated into a connector. Although the current connector designs can accommodate up to eight Bal-Seal® contacts, future connector designs will need to accommodate more contacts (e.g., 12-16). However, in order to accomplish this using Bal-Seal® contacts, the length of the connector would have to be increased, which may be unacceptable.

There, thus, remains a need for a lower-profile, high resolution connector for an electrical lead assembly.

SUMMARY OF THE INVENTION

In accordance with a first aspect of the present invention, an implantable connector for receiving an electrical lead body portion that carries an electrical terminal is provided. The implantable connector comprises an electrically insulative housing including an outer wall (e.g., a cylindrical wall) an interior cavity surrounded by the outer wall, a port through which the lead body portion can be introduced into the interior cavity, and a pair of first apertures disposed through the outer wall on a first side of the housing. The implantable connector further comprises an electrical spring clip contact mounted to the housing. The contact includes a common portion and a pair of legs extending from opposite ends of the common portion. The legs respectively extend through the first apertures into the interior cavity, such that the legs firmly engage the electrical terminal therebetween when the lead body portion is introduced into the interior cavity.

In one embodiment, the housing is less compliant than the contact, such that the housing does not deform when the legs firmly engage the terminal. In another embodiment, the portions of the legs within the interior cavity are radiused outward, such that the radiused portions at least partially wrap around the electrical terminal when the lead body portion is introduced into the interior cavity. In still another embodiment, the housing further comprises at least one opening disposed through the outer wall on a second side of the housing opposite the first side of the housing, wherein the legs extend from the interior cavity through the at least one opening. As one example, the opening(s) can comprise a pair of second apertures, in which case, the legs respectively extend from the interior cavity through the second apertures. As another example, the opening(s) can comprise an axial slot extending along a length of the outer wall, in which case, the legs extend from the interior cavity through the axial slot.

In yet another embodiment, the housing further includes a recess within an external surface of the housing between the first apertures, such that the common portion is seated within the recess. In this case, the recess may have a depth, such that the common portion does not extend above the external surface of the housing. The housing may further include at least one recess within an external surface of the housing adjacent the at least one opening, wherein ends of the legs are curved, such that they are seated within the at least one recess. In another embodiment, the implantable connector further comprises a tubular seal disposed within the housing around the interior cavity. The seal includes a pair of apertures that coincide within the first apertures, wherein the legs respectively extend through the apertures of the seal into the interior cavity of the receptacle. The implantable connector may further comprise an electrical conductor connected to the contact, and an electrically insulative cover disposed over the housing and common portion.

In another embodiment, the lead body portion carries a plurality of electrical terminals. In this case, the housing further includes a plurality of pairs of first apertures disposed through the outer wall, and axially spaced apart along a length of the housing. The implantable connector further comprises a plurality of electrical spring clip contacts mounted to the housing, with each of the contacts including a common portion and a pair of legs extending from opposite ends of the common portion. The legs of each contact respectively extend through a different pair of the first apertures into the interior cavity, such that the legs firmly engage a respective electrical terminal therebetween when the lead body portion is introduced into the interior cavity.

In accordance with a second aspect of the present inventions, an implantable lead assembly is provided. The implantable lead assembly comprises the lead body portion described above, and another electrical lead having another lead body portion and the connector carried by the other lead body portion.

In accordance with a third aspect of the present inventions, a method of manufacturing the connector comprising inserting the legs through the first apertures into the interior cavity. The method may further comprise inserting the legs from the interior cavity through at least one opening disposed through the outer wall on a second side of the housing opposite to the first side of the housing. The method may further comprise crimping each arm to form a radiused portion, such that the radiused portions are disposed within the interior cavity when the legs are respectively inserted through the first apertures. The method may further comprise introducing a tubular seal into the interior cavity, such that the legs are respectively introduced through a pair of apertures within the seal after the legs are introduced through the pair of first apertures in the outer wall. The method may further comprise applying an electrically insulative cover to an exterior surface of the housing.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 4 is a profile view of a distal end of a prior art stimulation lead used in the tissue stimulation system of FIG. 1;

FIG. 5 is a cross-sectional view of the stimulation lead of FIG. 4, taken along the line 5-5;

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
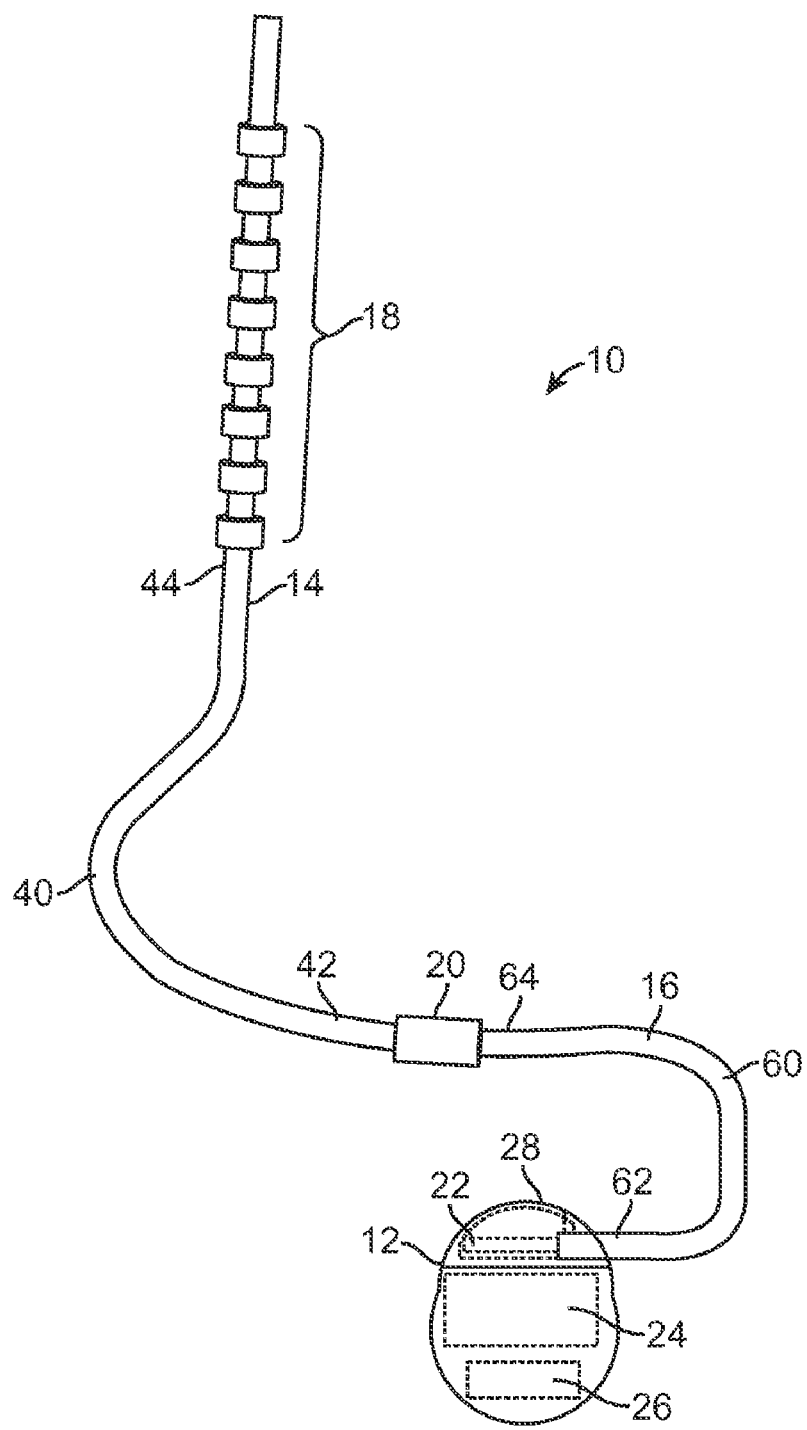
FIG. 1 is plan view of one embodiment of a prior art tissue stimulation system.
Figure 2:
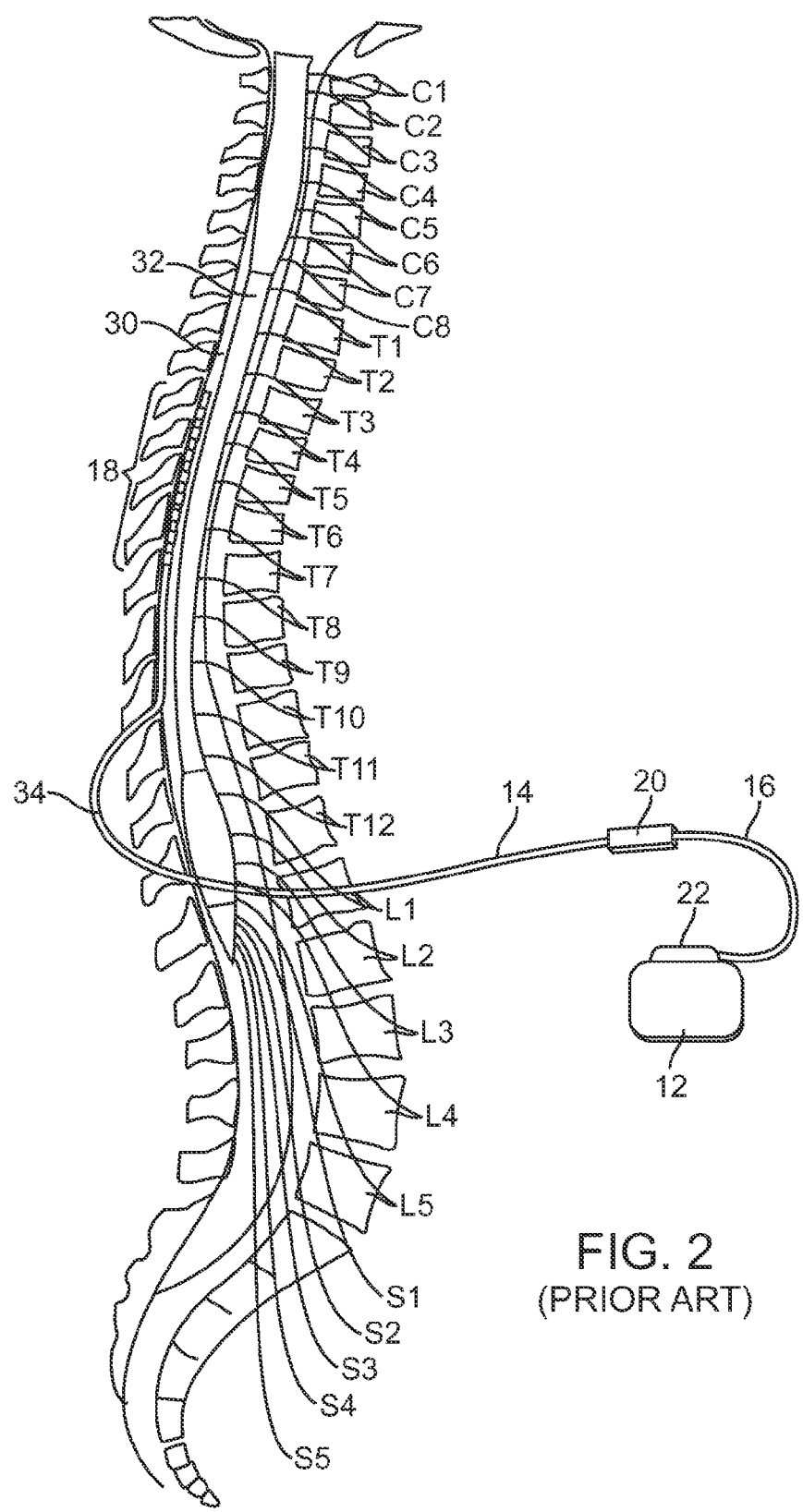
FIG. 2 is a plan view of the tissue stimulation system of FIG. 1 in use with a patient.

Referring first to FIGS. 1 and 2, a generalized tissue stimulation system 10 that may be used in spinal cord stimulation (SCS), as well as other stimulation applications, will be described. The stimulation system 10 generally comprises an implantable neurostimulator 12, an implantable stimulation lead 14, which carries an array of electrodes 18, and an implantable extension lead 16. Although only one stimulation lead 14 is shown, more than one stimulation lead, and typically two stimulation leads, can be used in the stimulation system 10. As there shown, the proximal end of the stimulation lead 14 is removably mated to the distal end of the extension lead 16 via a connector 20 associated with the extension lead 16, and the proximal end of the extension lead 16 is removably mated to the neurostimulator 12 via a connector 22 associated with the neurostimulator 12.

In the illustrated embodiment, the neurostimulator 12 takes the form of an implantable pulse generator (IPG) that comprises an electronic subassembly 24 (shown in phantom), which includes control and pulse generation circuitry (not shown) for delivering electrical stimulation energy to the electrodes (described below) of the stimulation lead 14 in a controlled manner, and a power supply, e.g., a battery 26 (shown in phantom), so that once programmed and turned on by an external programming device (not shown), the neurostimulator 12 can operate independently of external hardware.

Alternatively, the neurostimulator 12 can take the form of an implantable receiver-stimulator (not shown), in which case, the power source, e.g., a battery, for powering the implanted receiver, as well as control circuitry to command the receiver-stimulator, will be contained in an external controller inductively coupled to the receiver-stimulator via an electromagnetic link. Alternatively, the neurostimulator 12 can take the form of an external trial stimulator (ETS) (not shown), which has similar pulse generation circuitry as an IPG, but differs in that it is a non-implantable device that is used on a trial basis after the stimulation lead 14 has been implanted and prior to implantation of the IPG, to test the responsiveness of the stimulation that is to be provided.

The neurostimulator 12 comprises an outer housing 28 for housing the electronic and other components (described in further detail below), and the connector 22 to which the proximal end of the stimulation lead 14 (or optionally the proximal ends of the extension leads 16) mates in a manner that electrically couples the electrodes 18 to the pulse generation circuitry contained within the outer housing 28. The outer housing 28 may be composed of a biocompatible material, such as titanium, and forms a hermetically sealed compartment wherein the electronic subassembly 24 and battery 26 are protected from the body tissue and fluids. The connector 22 is disposed in a portion of the housing 28 that is, at least initially, not sealed.

As will be described in further detail below, the connector 22 carries a plurality of contacts that come into electrical contact with the respective terminals (described in further detail below) of the stimulation lead 14 or extension lead 16 when the proximal end of the stimulation lead 14 or extension lead 16 is inserted into the connector 22. Electrical conductors (not shown), which extend from the connector 22 in electrical contact with the contacts, penetrate the housing 28 into the sealed chamber and connect to the electronic subassembly 24. Additional details discussing neurostimulators, including the outer housing 28 and connector 22, are disclosed in U.S. patent application Ser. No. 11/327,880, entitled "Connector and Methods of Fabrication," which is expressly incorporated herein by reference.

As shown in FIG. 2, the stimulation lead 14 is implanted in the epidural space 30 of a patient in close proximity to the spinal cord 32. Because of the lack of space near the lead exit point 34 where the stimulation lead 14 exits the spinal column, the neurostimulator 12 is generally implanted in a surgically-made pocket either in the abdomen or above the buttocks. The neurostimulator 12 may, of course, also be implanted in other locations of the patient's body. Use of the extension lead 16 facilitates locating the neurostimulator 12 away from the lead exit point 34. In addition, in some cases, the extension lead 16 may serve as a lead adapter if the proximal end of the stimulation lead 14 is not compatible with the connector of the neurostimulator 12 (e.g., different manufacturers use different connectors at the ends of their stimulation leads and are therefore not compatible with the connector heads of the neurostimulator of another manufacturer). The extension lead 16 may be made to adapt the stimulation lead 14 to connect the neurostimulator 12 to the stimulation lead 14, and hence, "adapt" the stimulation lead 14 to the neurostimulator 12.

Figure 3:
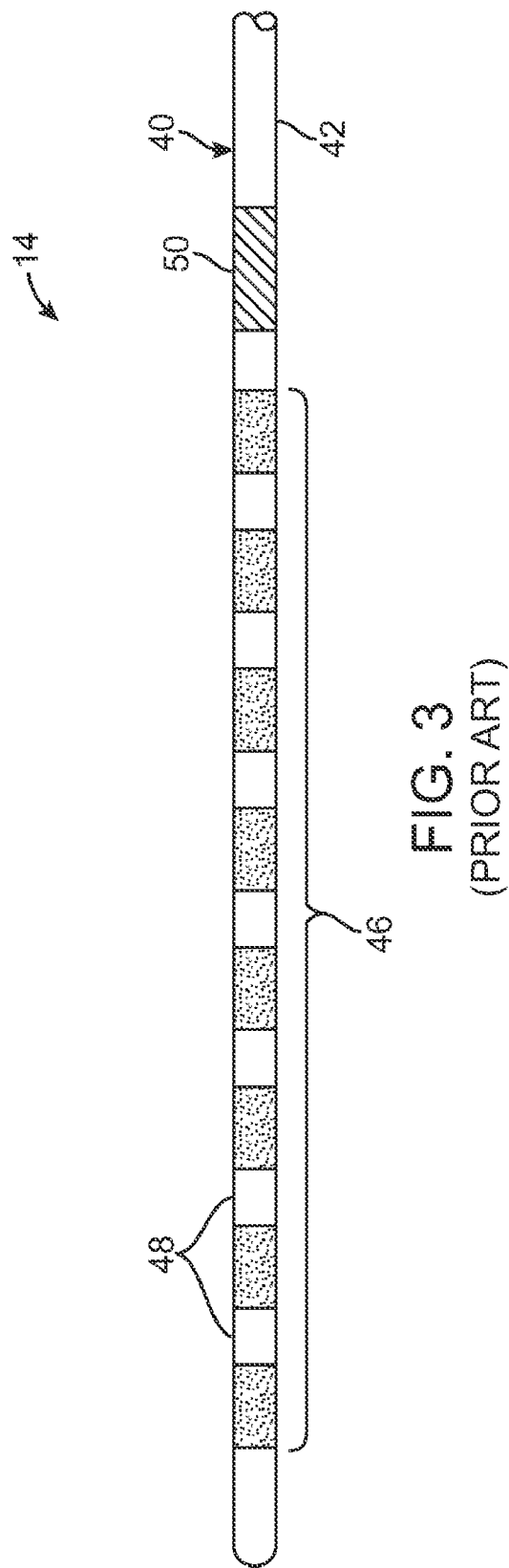
FIG. 3 is a profile view of a proximal end of a prior art stimulation lead used in the tissue stimulation system of FIG. 1.

Referring further to FIGS. 3 and 4, the stimulation lead 14 comprises an elongated lead body 40 having a proximal end 42 and a distal end 44. The lead body 40 may, e.g., have a diameter of between about 0.03 inches to 0.07 inches and a length within the range of 30 cm to 90 cm for spinal cord stimulation applications. The lead body 40 may be composed of a suitable electrically insulative material, such as, a polymer (e.g., polyurethane or silicone), and may be extruded from as a unibody construction.

The stimulation lead 14 further comprises a plurality of terminals 46 mounted to the proximal end 42 of the lead body 40 (FIG. 3), and the plurality of electrodes 18 mounted to the distal end 44 of the lead body 40 (FIG. 4). In the illustrated embodiment, the stimulation lead 14 is a percutaneous lead, and to this end, the electrodes 18 are arranged in-line along the lead body 40. In an alternative embodiment, the stimulation lead may take the form of a single paddle lead (not shown), in which case the electrodes 18 may be arranged in a two-dimensional pattern on one side of a paddle. Further details regarding the construction and method of manufacture of paddle leads are disclosed in U.S. patent application Ser. No. 11/319,291, entitled "Stimulator Leads and Methods for Lead Fabrication," the disclosure of which is expressly incorporated herein by reference.

Although the stimulation lead 14 is shown as having sixteen terminals 46 (FIG. 3) and sixteen corresponding electrodes 18 (FIG. 4), the number of terminals and electrodes may be any number suitable for the application in which the stimulation lead 14 is intended to be use (e.g., two, four, sixteen, etc.). Each of the terminals 46 and electrodes 18 takes the form of a cylindrical ring element composed of an electrically conductive, biocompatible, non-corrosive, material, such as, e.g., platinum, titanium, stainless steel, or alloys thereof.

The stimulation lead 14 further includes a plurality of electrically insulative spacers 48 located on the lead body 40 between the respective terminals 46 and electrodes 18. The spacers 48 may be composed of a suitable material, such as, a polymer (e.g., polyurethane or silicone). The stimulation lead 14 further includes an optional retention sleeve 50 located at the proximal end 42 of the lead body 40 just distal to the terminals 46. The retention sleeve 50 serves as a hard surface for a mechanical securing element, such as a set screw (not shown), used to secure the proximal end of the stimulation lead 14 within a connector (e.g., either carried by the extension lead or the neurostimulator). The stimulation lead 14 further comprises an optional radiopaque marker 52 located at the distal tip of the lead body 40.

As shown in FIG. 5, the stimulation lead 14 also includes a plurality of electrical conductors 54 (each comprising individual strands 56) extending through individual lumens 57 within the lead body 40 and connected between the respective terminals 46 and electrodes 18 using suitable means, such as welding, thereby electrically coupling the proximally-located terminals 46 with the distally-located electrodes 18. In the illustrated embodiment, the conductor 54 is a multfilar cable (1×19 or 1×7) wire made from 28% inner core of pure silver with 78% outer cladding of MP35N stainless steel. The conductor 54 is then insulated with a thin outer jacket (0.001" thick) of Ethylene Tetrafluoroethylene (ETFE) fluoro-based polymer. In the illustrated embodiment, the conductors 54 can be pre-cut and two zones on the ETFE insulation pre-ablated where they are connected between the respective electrode 18 and terminal 46. The stimulation lead 14 further includes a central lumen 58 that may be used to accept an insertion stylet (not shown) to facilitate lead implantation.

Further details describing the construction and method of manufacturing stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Referring back to FIG. 1, the extension lead 16 is similar to the stimulation lead 14 in that it comprises an elongated lead body 60 having a proximal end 62 and a distal end 64, and a plurality of terminals (not shown) mounted to the proximal end 62 of the lead body 60. The lead body 60 of the extension lead 16 may be similarly dimensioned and constructed as the lead body 40 of the stimulation lead 14. The extension lead 16 may also include retention sleeve (not shown) much like the retention sleeve 50 of the stimulation lead 14.

The extension lead 16 differs from the stimulation lead 14 in that, instead of electrodes, it comprises the previously mentioned connector 20 mounted to the distal end 64 of the lead body 60. The connector 20 is configured to accept the proximal end 42 of the stimulation lead 14. As will be described in further detail below, the connector 20 carries a plurality of contacts that come into electrical contact with the respective terminals 46 of the stimulation lead 14 when the proximal end 42 of the stimulation lead 14 is inserted into the connector 20. In a similar manner as the stimulation lead 14 (shown in FIG. 5), the extension lead 16 also includes a plurality of electrical conductors extending through individual lumens (both not shown) within the lead body 60 and connected between the respective terminals and contacts using suitable means, such as welding, thereby electrically coupling the proximally-located terminals with the distally-located contacts.

Referring now to FIGS. 6-12, one embodiment of a connector 100 that can be incorporated into the extension lead 16 and/or neurostimulator 12 (shown in FIGS. 1 and 2) will be described. As will be described in further detail below, the connector 100 can receive the proximal end of an electrical lead, which can be firmly engaged and locked within the connector 100. The electrical lead may be, e.g., the stimulation lead 14 or the extension lead 16 (shown in FIGS. 1 and 2), depending on whether an extension lead is used in the lead assembly and whether the connector 100 is incorporated into an extension lead or in a neurostimulator. That is, if the connector 100 is to be located in an extension lead, the electrical lead that is mated within the connector 100 will be the stimulation lead. If the connector 100 is to be located in a neurostimulator, the electrical lead that is mated within the connector 100 will be the extension lead if used in the lead assembly and will be the stimulation lead if the extension lead is not used in the lead assembly.

The connector 100 generally comprises (1) an electrically insulative housing 102 for receiving the proximal end of the electrical lead; (2) a plurality of electrical spring clip contacts 104 (in this case, sixteen contacts) incorporated into the housing 102, such that contacts 104 firmly engage the terminals of an electrical lead that is received into the housing 102; (3) an electrically insulative seal 106 to ensure that the contacts 104, and thus the terminals in engagement with the contacts 104, are electrically isolated from each other; (4) a connector block 108 associated with the housing 102 to lock the electrical lead within the housing 102; (5) a plurality of electrical conductors (not shown) connected to the respective contacts 104; and (6) an optional electrically insulative covering (not shown) disposed over the housing 102.

Referring further to FIGS. 13-16, the housing 102 (shown in phantom in FIG. 10) includes an outer wall 110, an interior passage 112 (shown best in FIGS. 15 and 16) circumferentially surrounded by the outer wall 110, a port 114 (shown best in FIGS. 13-15) into which the proximal end of the electrical lead can be introduced, and an end cap 116 opposite the port 114, which serves as an insertion stop for the electrical lead. In the illustrated embodiment, the outer wall 110 takes the form of a cylinder having an open end that forms the port 114 and a closed end that forms the end cap 116. The dimensions and composition of the outer wall 110 are preferably selected, such that the housing 102 is less compliant than the contacts 104 that are to be mounted in the housing 102, such that the housing 102 does not substantially deform when the contacts 104 engage the terminals of the electrical lead, thereby maintain the spacing and orientation of the contacts 104 relative to each other, as will be described in further detail below. For example, the length of the outer wall 110 may be in the range of 1-2 inches, the outer diameter of the outer wall 110 may be in the range of 0.18-0.20 inches, the thickness of the outer wall 110 may be in the range of 0.025-0.040 inches, and the material from which the outer wall 110 is composed may be polycarbonate or polyetheretherketone (PEEK).

To accommodate the contacts 104, the housing 102 includes a pattern of apertures and recesses formed within the outer wall 110 using suitable means, such as laser ablation or molding.

Figure 13:
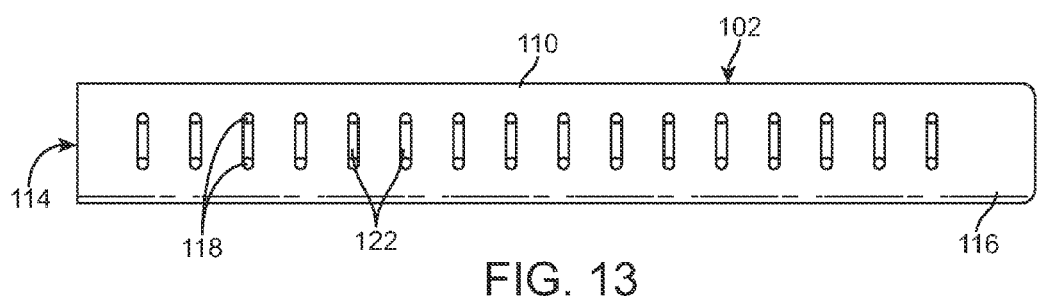
FIG. 13 is a top view of an outer housing used in the connector of FIG. 6.
Figure 14:
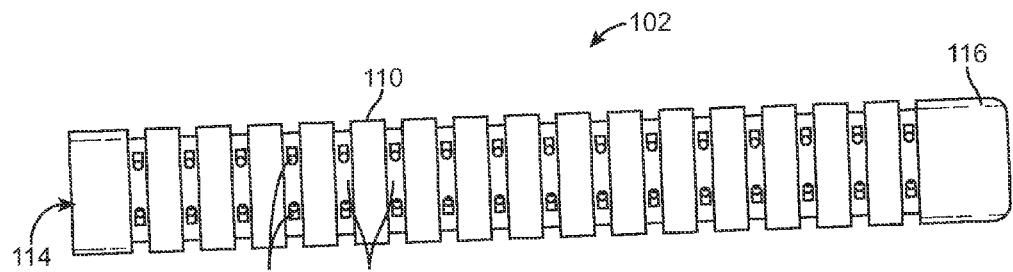
FIG. 14 is a bottom view of the outer housing of FIG. 13.
Figure 15:
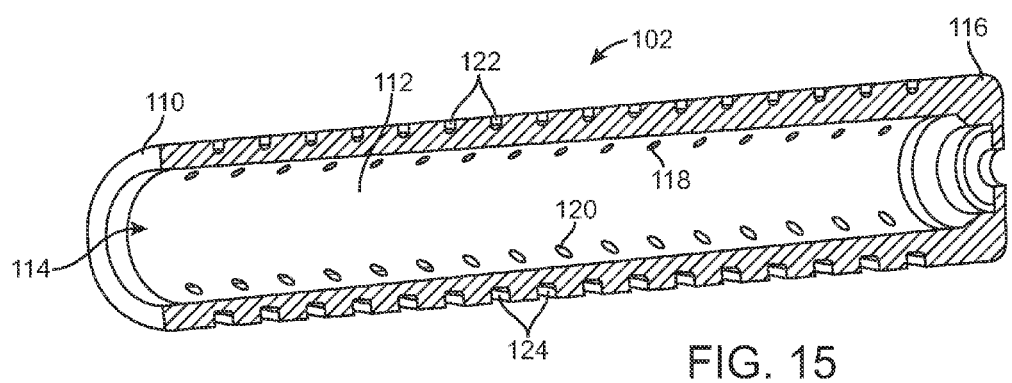
FIG. 15 is a cross-sectional view of the outer housing of FIG. 13.
Figure 16:
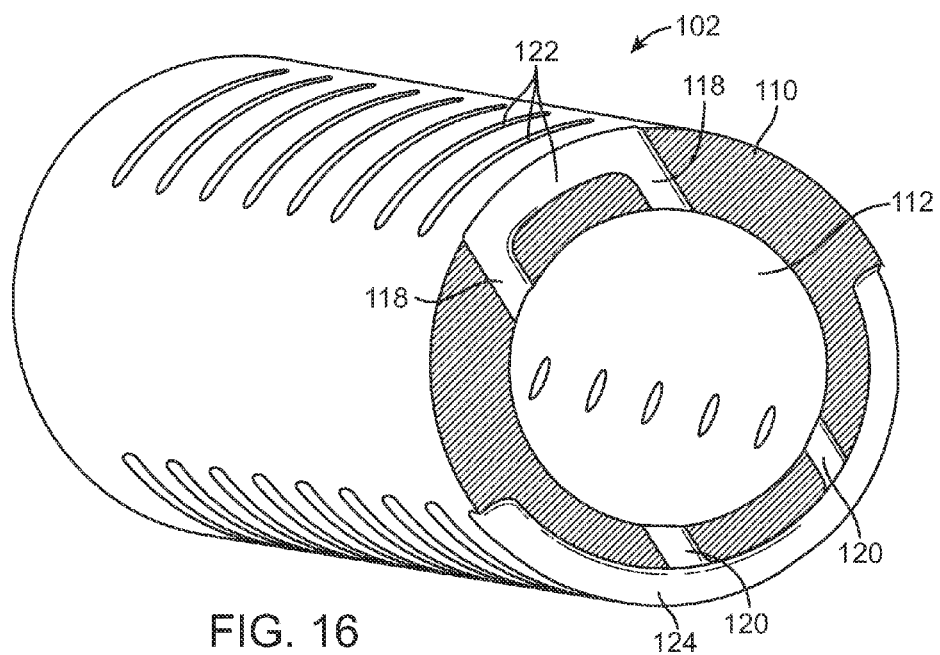
FIG. 16 is a cross-sectional perspective view of the outer housing of FIG. 13.

In particular, the housing 102 includes pairs of contact entry apertures 118 (best shown in FIGS. 13, 15, and 16) extending through the outer wall 110. The aperture 118 of each pair are circumferentially spaced from each other a specific distance, which as will be described in further detail below will depend on the dimensions of the contacts 104. The apertures 118 of each pair are also axially aligned with each other (i.e., they are disposed along the axis of the outer housing 102 the same distance). The aperture pairs 118 are axially spaced from each other a specific distance. In the illustrated embodiment, the axial spacing is uniform between the respective aperture pairs 118, although in alternative embodiments, the axial spacing between the respective aperture pairs 118 may be non-uniform. The axial spacing will ultimately depend on the length of the outer wall 110 and the number of contacts 104 that will be incorporated into the connector 100. The aperture pairs 118 are also circumferentially aligned with each other (i.e., they are clocked around the axis the same angle). For example, as illustrated in FIG. 13, the aperture pairs 18 are all shown at the top of the outer wall 110 (or the 12 o'clock position). In alternative embodiments, the aperture pairs 118 may be circumferentially misaligned or staggered.

The housing 102 further includes pairs of contact exit apertures 120 (best shown in FIGS. 14, 15, and 16) extending through the outer wall 110. Like the contact entry apertures 118, the contact exit apertures 120 of each pair are circumferentially spaced from each other a specific distance, and in particular, the same distance as the contact entry apertures 118 are circumferentially spaced from each other. The contact exit apertures 120 of each pair are also axially aligned with each other. The aperture pairs 120 are axially spaced from each other the same distance as the contact entry aperture pairs 120, and are circumferentially opposite the respective entry aperture pairs 118 (i.e., each corresponding contact entry aperture pair 118 and contact exit pair 120 are clocked from each other 180 degrees). Thus, because the contact entry aperture pairs 118 are circumferentially aligned, the contact exit aperture pairs 120 are likewise circumferentially aligned.

The housing 102 further includes a channeled recess 122 (best shown in FIGS. 13 and 16) formed in the exterior surface of the outer wall 110 adjacent each contact entry aperture pair 118, and a channeled recess 124 (best shown in FIGS. 14 and 16) formed in the exterior surface of the outer wall 110 adjacent each contact exit aperture pair 124. In the illustrated embodiment, each channeled recess 122 circumferentially extends between contact entry apertures 118 of each respective pair, and each channeled recess 124 circumferentially extends between and outwardly away from the contact exit apertures 120 of each respective pair. In alternative embodiments, two channeled recesses (not shown) may circumferentially extend away from the contact exit apertures 120 of each respective pair (i.e., there is no recess between the contact exit apertures 120) or the channeled recess may only extend between the contact exit apertures 120.

Figure 17:
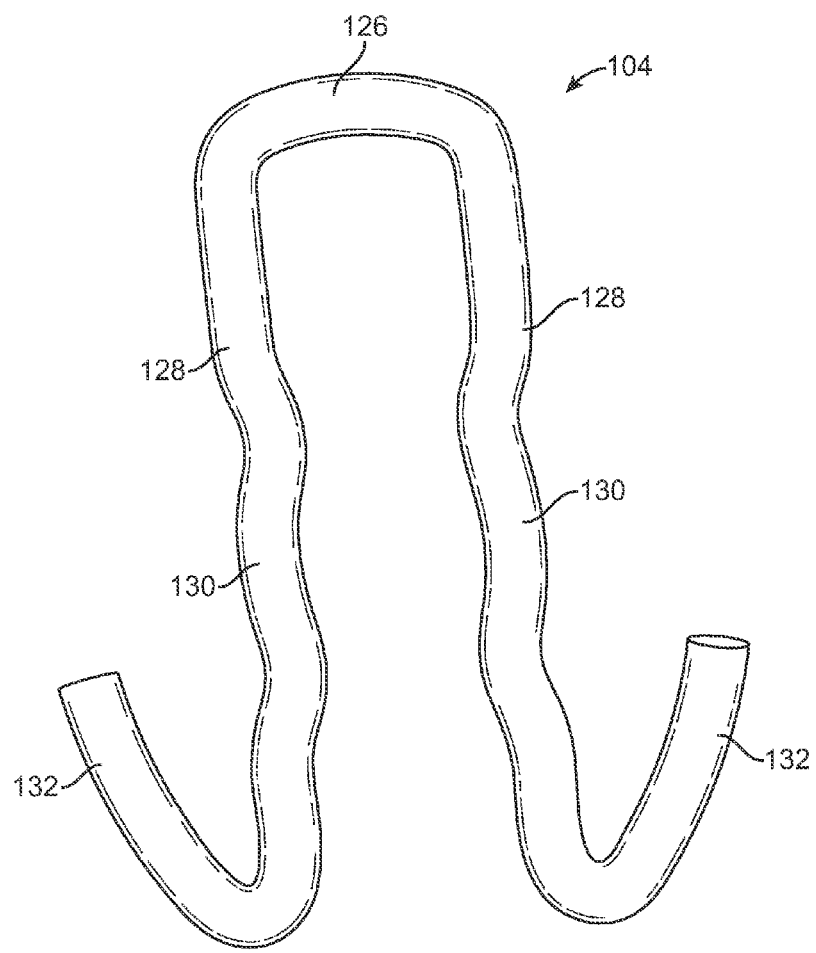
FIG. 17 is a perspective view of an electrical spring clip contact used in the connector of FIG. 6.

Referring to FIG. 17, each of the contacts 104 is formed from a cylindrical wire composed of a suitably electrically conductive and resilient material, such as platinum, titanium, stainless steel, or alloys thereof. For example, the contacts 104 may be composed of platinum-iridium alloy (90% Pt-10% Iridium), MP35N nickel-steel, and 316 stainless steel. The diameter of the wire from which each contact 104 is formed is preferably of a suitable size to provide the necessary spring force to firmly engage the respective terminal. For example, the wire can have a diameter in the range of 0.008-0.015 inches. Significantly, the relatively small diameter of the wire used to make the contacts 104, as compared to Bal-Seal® contacts (which have a length of 0.055 inches), allows many more electrical contacts to be incorporated into the connector 100 at a much cheaper cost.

Each of the contacts 104 includes a common portion 126 and a pair of legs 128 extending downward from opposite ends of the common portion 126. The length of the common portion 126 equals the distance between the contact entry apertures 118 of each pair, such that the axes of the legs 128 will coincide with the contact entry apertures 118. The length of each of the respective legs 128 is greater than the distance between the corresponding apertures 118, 120 through the interior passage 112, such that the legs 128 can completely extend through the interior passage 112.

As shown in FIGS. 7-9 and 11, the legs 128 of each contact 104 extend through a respective pair of contact entry apertures 118 into the interior passage 112 of the housing 102, such that the common portion 126 of the respective contact 104 is seated within the recess 122 extending between the contact entry apertures 118, and the middle portions 130 of the legs 128 firmly engage the respective electrical terminal (not shown) therebetween when the proximal end of the electrical lead is introduced into the internal passage 112. In the illustrated embodiment, the middle portions 130 of the legs 128 are radiused outward, such that the middle portions 130 at least partially wrap around the electrical terminal when the lead body portion is introduced into the interior passage 112. As a result, a greater contact surface between the contact 104 and the respective terminal is achieved, thereby providing a more secure engagement therebetween.

The legs 128 of each contact 104 further extend from the interior passage 112 of the housing 102 and through the contact exit apertures 120, such that end portions 132 of the legs 128 are disposed externally to the outer housing 102. The end portions 132 of the legs 128 are curved outward back towards the common portion 126, such that they are seated within the recess 124 extending outwardly from the contact exit apertures 120. In the alternative case where there is a recess only between the contact exit apertures 120, the end portions 132 of the legs 128 (if made shorter) can be curved inward towards each other, such that they are both seated in the recess. The end portions 132 of the legs 128 may be curved using suitable means, such as a crimping tool. Preferably, the depth of the recesses 122, 124 is equal to or greater than diameter of the wire from which the contact 104 is formed, so that no portion of the common portions 126 or legs 128 extends above the external surface of the outer wall 110.

Figure 10:
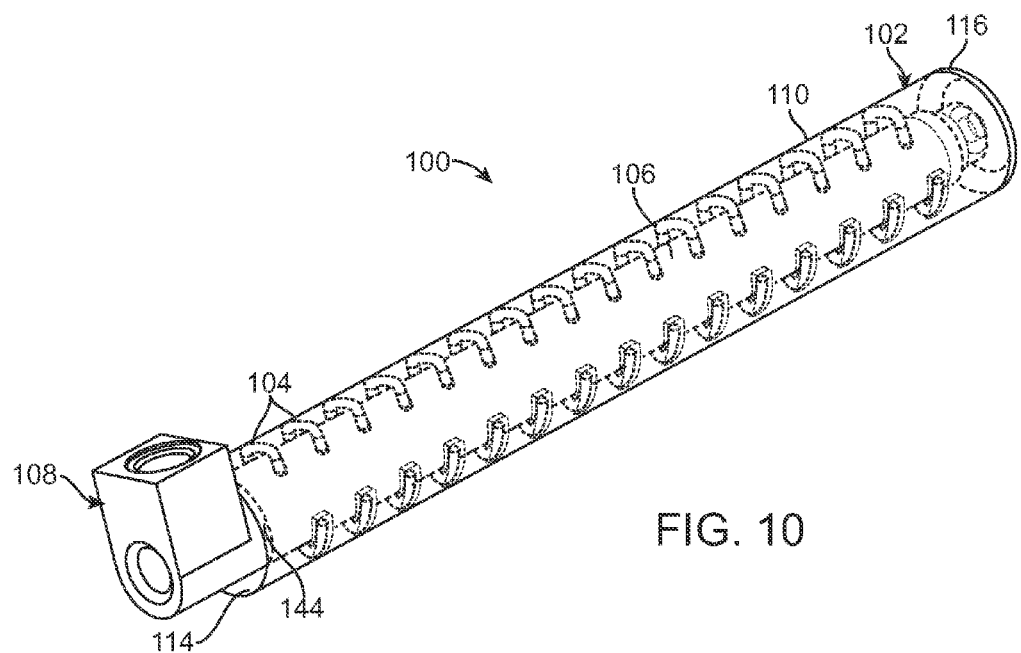
FIG. 10 is a perspective view of the connector of FIG. 6, particularly showing an outer housing of the connector in phantom.
Figure 11:
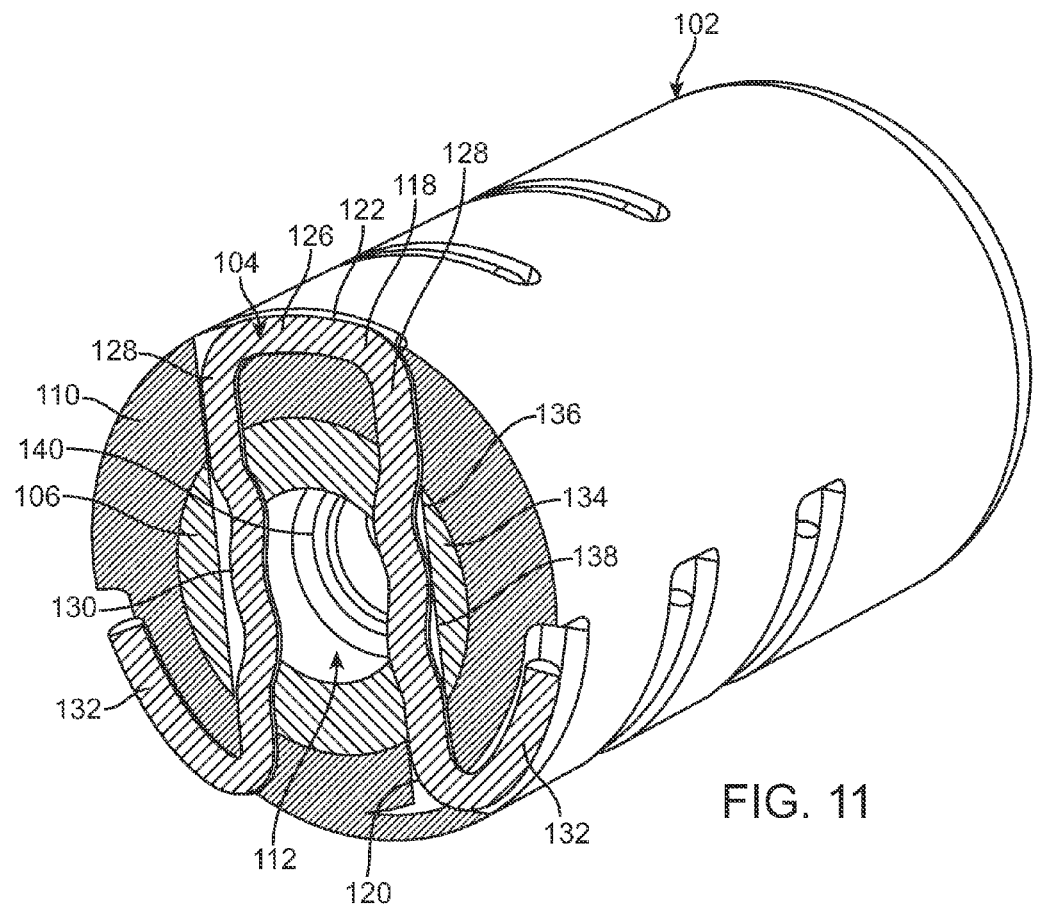
FIG. 11 is a cross-sectional view of the connector of FIG. 6.
Figure 12:
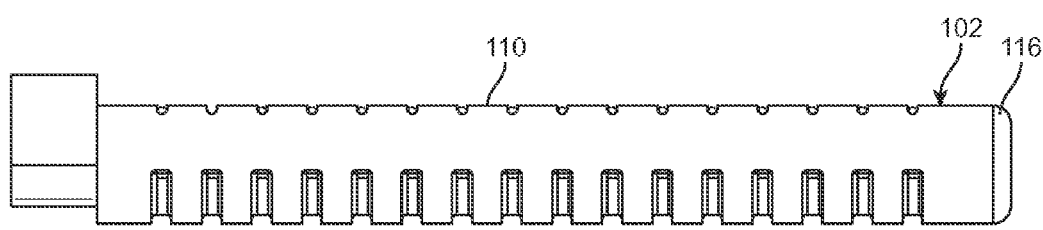
FIG. 12 is a side view of the connector of FIG. 6.

Referring to FIGS. 10 and 11, the tubular seal 106 is disposed within the housing 102, and in particular, is interference fit with the interior surface of the housing 102, such that seal 106 surrounds the interior passage 112. The tubular seal 106 may be composed of any electrically insulative and compliant material, such as silicone.

Figure 18:
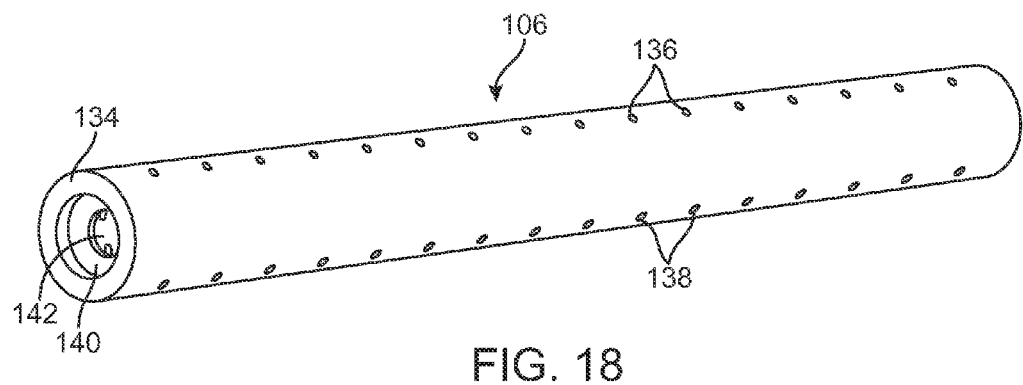
FIG. 18 is a perspective view of a tubular seal used in the connector of FIG. 6.
Figure 19:
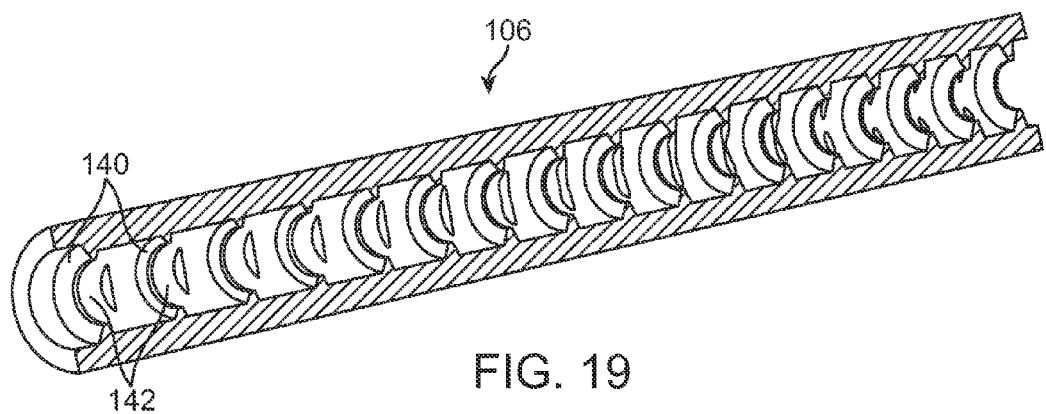
FIG. 19 is a cross-sectional view of the tubular seal of FIG. 18.

Referring further to FIGS. 18 and 19, the tubular seal 106 includes a cylindrical wall 134 having a diameter substantially the same as the inner diameter of the housing 102, such that the tubular seal 106 is snugly fit within the interior passage 112 of the housing 102. The tubular seal 106 includes pairs of contact entry apertures 136 (only one shown) that are coincident with the pairs of contact entry apertures 118 (shown in FIG. 13) of the housing 102, and pairs of contact exit apertures 138 (only one shown) that are coincident with the pairs of contact exit apertures 120 (shown in FIG. 14) of the housing 102. Thus, the legs 128 of each contact 104 extend from the contact entry apertures 118 of the housing 102, through the contact entry apertures 136 of the seal 106, and into the interior passage 112. The legs 128 of each contact 104 also extend from the interior passage 112, through the contact exit apertures 138 of the seal 106, and then through the contact exit apertures 122 of the housing 102.

Notably, as best shown in FIG. 11, the contact entry apertures 136 and contact exit apertures 138 of the seal 106 are smaller than the diameter of wire from which the respective contact 104 is composed, such that the apertures 136, 138 conform to, and thereby seal, against the outer surface of the contacts 104. As a result, electrical isolation between the contacts 104, and therefore the terminals of the lead (not shown), is increased. To further maximize isolation between the electrical contacts 104, the seal 106 further includes a plurality of inner annular flanges 140 that extend along the length of the seal 106 into the interior passage 112 between the respective contacts 104, such that when the proximal end of the electrical lead is inserted into the interior passage 112 and through center openings 142 in the annular flanges 140, the annular flanges 140 will conform to, and thereby seal, against the outer surface of the electrical lead. As a result, even if an electrolytic fluid enters the interior passage 112 of the outer housing 102, the annular flanges 140 will prevent or, at least minimize, the leakage of electrical current between the contacts 104.

Figure 20:
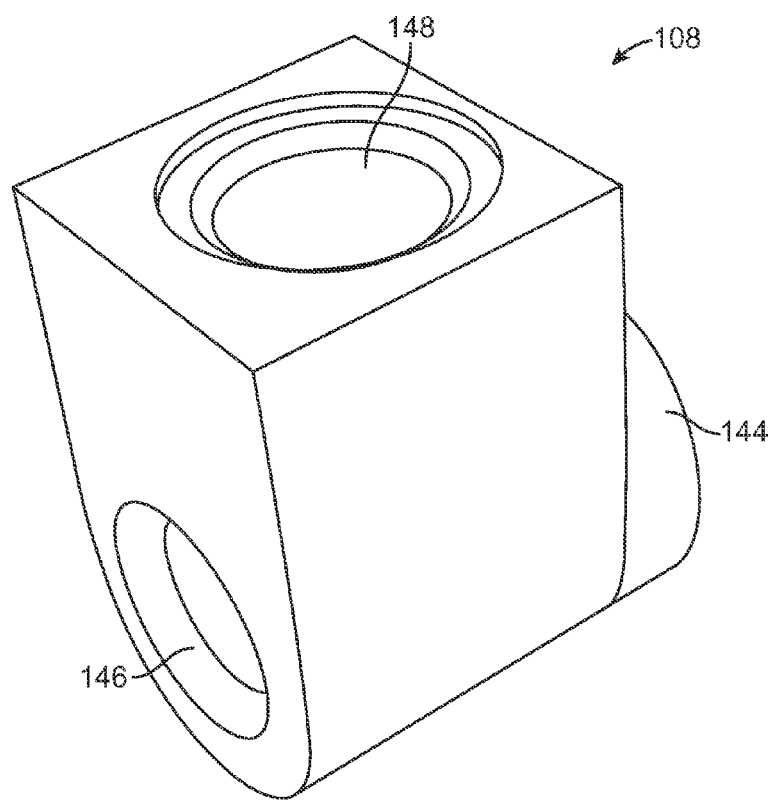
FIG. 20 is a perspective view of a connector block used in the connector of FIG. 6.

Referring to FIG. 20, the connector block 108 serves a rigid platform for supporting the forces applied to the set screw. To this end, connector block 108 includes an annular flange 144 that is mounted within the port 114 of the housing 102 (best shown in FIG. 10) using suitable means, such as bonding, and a bore 146 leading to the annular flange 144 into the port 114 of the outer housing 102. Thus, the proximal end of the electrical lead can be inserted through the bore 146 of the connector block 108 and into the port 114 of the housing 102. The connector block 108 further includes a threaded bore 148 disposed orthogonally to the bore 146. A tool (e.g., a torque wrench) may be inserted into the threaded bore 148 to tighten or loosen a set screw (not shown) that can be used to firmly secure the electrical lead (e.g., by frictionally engaging a retention sleeve 50 shown in FIG. 3) within the outer housing 102. The connector block 108 can be composed of any suitable conductor or non-conductive material, such as, e.g., non-conductive polymers, polyetheretherketone (PEEK), ceramics, etc., metal, alloys, conductive polymers, conductive carbon, etc.

The electrical conductors (not shown) are respectively connected to the contacts 104 using suitable techniques known in the art, such as welding. If the connector 100 is incorporated into an electrical lead, such as an extension lead, the electrical conductors take the form of wires that are routed through the housing 102 (e.g., the electrical conductors 54 shown in FIG. 5) and then through a lead body (not shown) that extends from the connector 100. If the connector 100 is incorporated into a neurostimulator, the electrical conductors extend out from corresponding openings (not shown) made in the housing 102.

The electrically insulative cover (not shown) may be composed of a suitably electrically insulative material (such as, e.g. silicone or polyurethane). The cover is disposed over the housing 102 in such a manner that all exposed surfaces of the contacts 104 are covered, and thereby electrically insulated from each other if the connector 100 comes in contact with tissue or fluids.

Figure 6:
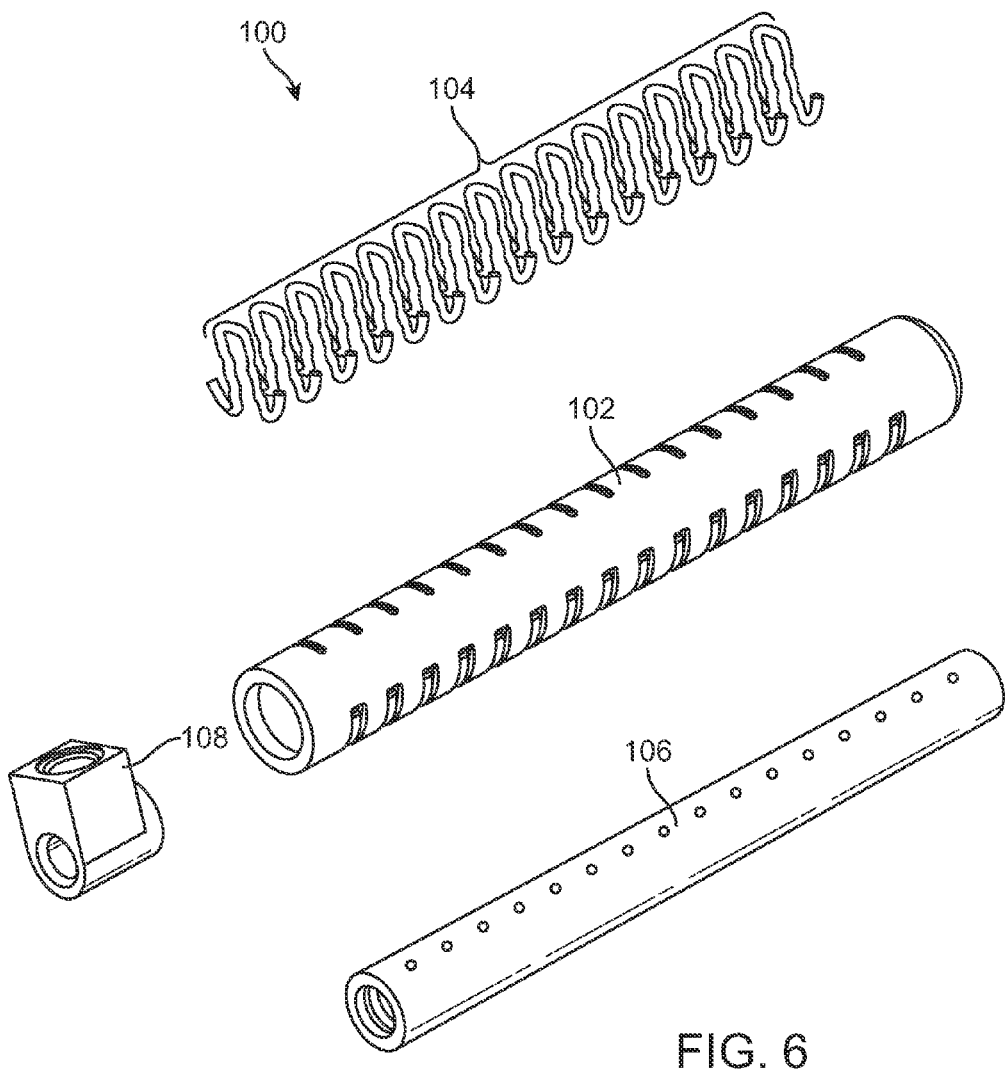
FIG. 6 is an exploded view of one embodiment of a connector constructed in accordance with the present inventions, which can be used in the tissue stimulation system of FIG. 1.
Figure 7:
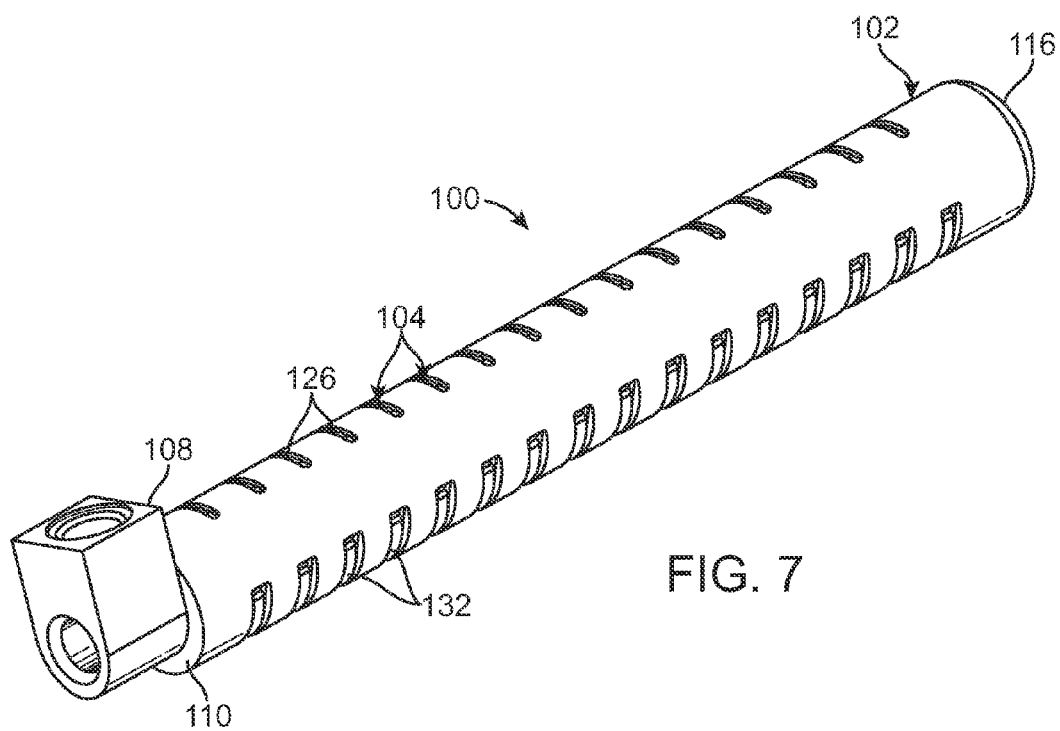
FIG. 7 is one perspective view of the connector of FIG. 6.
Figure 8:
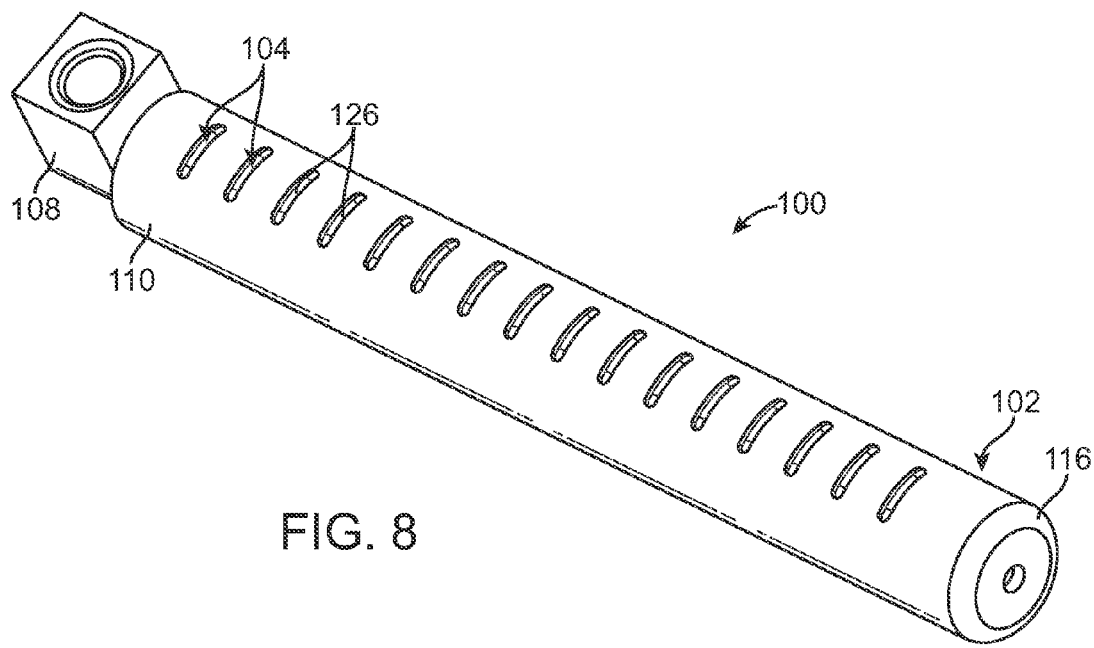
FIG. 8 is another perspective view of the connector of FIG. 6.
Figure 9:
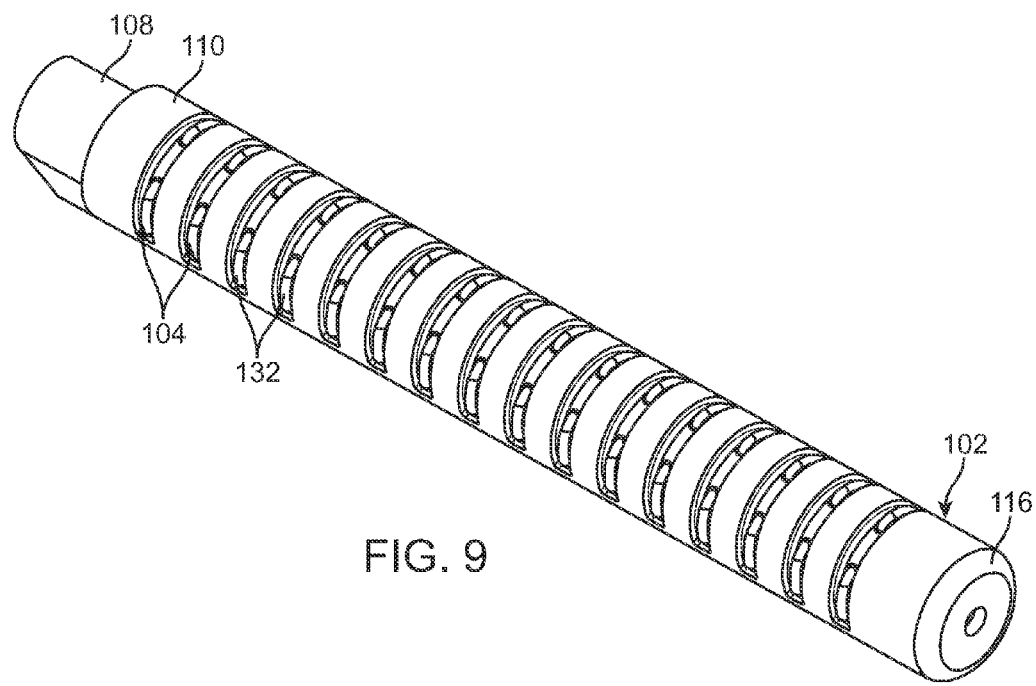
FIG. 9 is still another perspective view of the connector of FIG. 6.
Figure 21:
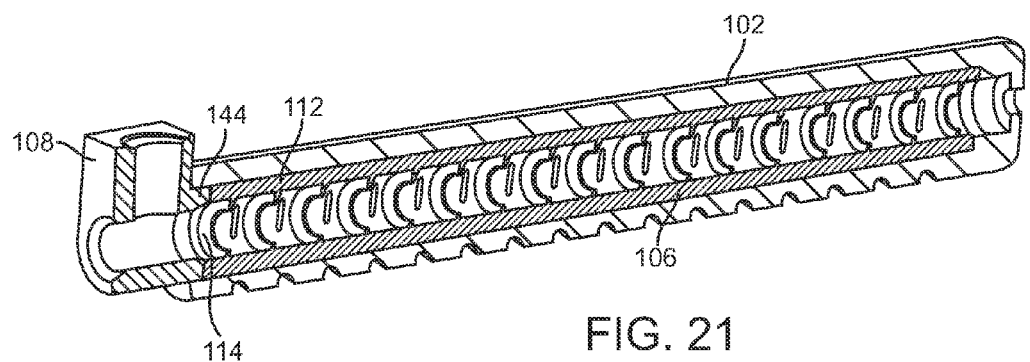
FIG. 21 is a cross-sectional view a subassembly of the connector of FIG. 6, particularly showing the outer housing, tubular seal, and connector block.
Figure 22:
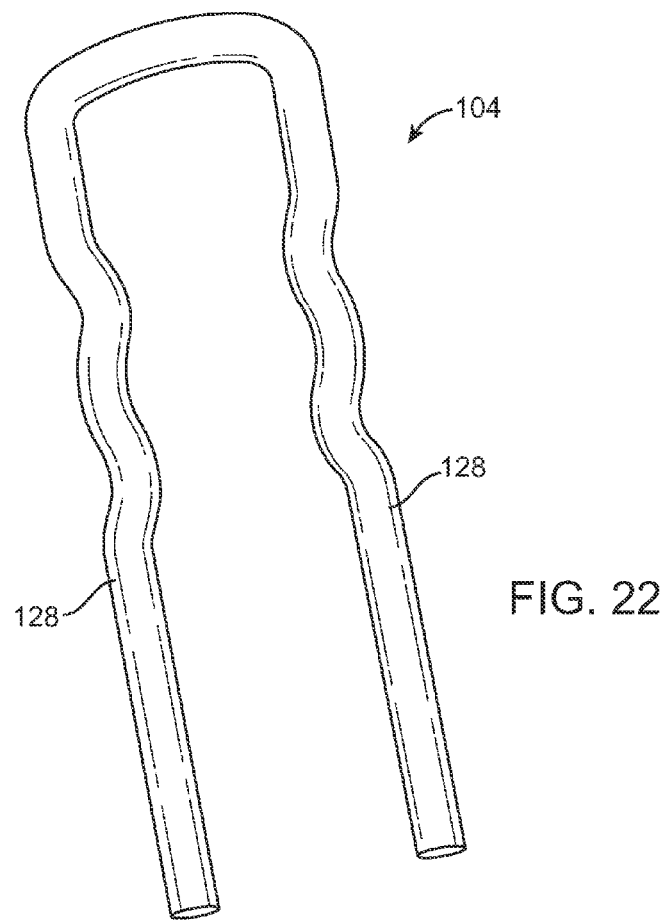
FIG. 22 is a perspective view of the electrical spring clip contact of FIG. 17, particularly showing the distal ends of the legs uncrimped.
Figure 23:
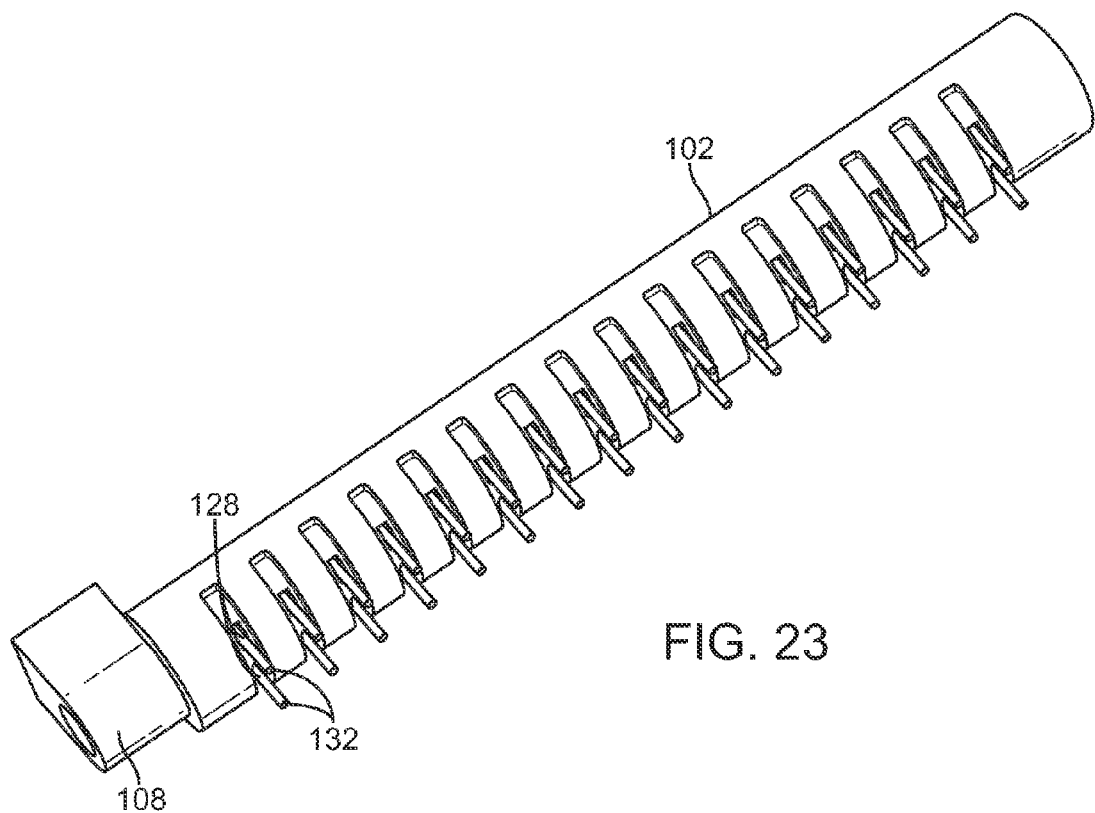
FIG. 23 is a perspective view of a subassembly of the connector of FIG. 6, particularly showing the outer housing, tubular seal, connector block, and uncrimped pins.

Referring to FIGS. 21-23, a method of assembling the components illustrated in FIG. 6 into the connector 100 illustrated in FIGS. 7-12 will now be described. First, as illustrated in FIG. 21, the seal 106 is inserted into the interior passage 112 of the housing 102 via the port 114, such that the seal 106 and housing 112 are interference fit with each other, and the annular flange 144 of the connector block 108 is inserted into the port 114, such that the annular flange 144 abuts the seal 106. The annular flange 144 of the connector block 108 may be affixed within the port 114 via suitable means, such as bonding. Next, each contact 104, in its uncrimped form (shown in FIG. 22), is incorporated into the housing 112. In particular, as shown in FIG. 11, the legs 128 of each contact 104 are inserted through the corresponding entry apertures 118 in the housing 102, through the corresponding entry apertures 136 in the seal 106, through the interior passage 112, through the corresponding exit apertures 138 in the seal 106, and out the corresponding exit apertures 120 in the housing 102. As shown in FIG. 23, the end portions 132 of the respective legs 128 of each contact 104 extend from the housing 102. Next, the end portions 132 of the arms 128 of each contact 104 are crimped away from each other until seated within the recess 124, as illustrated in FIGS. 9 and 11. Then, the electrical conductors (such as the electrical conductors 58 shown in FIG. 5) would be attached (e.g., via welding) to the contacts 104. Next, the exterior surface of the housing 102 is overmolded with the electrically insulative cover (not shown).

Referring now to FIGS. 24-28, another embodiment of a connector 200 that can be incorporated into the extension lead 16 and/or neurostimulator 12 (shown in FIGS. 1 and 2) will be described. Like the connector 100, the connector 200 can receive the proximal end of an electrical lead, which can be firmly engaged and locked within the connector 200. Again, the electrical lead may be, e.g., the stimulation lead 14 or the extension lead 16 (shown in FIGS. 1 and 2). In contrast to the connector 100, the connector 200 has a discrete end cap and allows for the seal to be laterally introduced into the housing, as well as allows for easier injection molding of the housing (no blind core pins).

The connector 200 generally comprises (1) an electrically insulative housing 202 for receiving the proximal end of the electrical lead; (2) the previously described plurality of electrical spring clip contacts 104 (in this case, sixteen contacts) incorporated into the housing 202, such that contacts 104 firmly engage the terminals of an electrical lead that is received into the housing 202; (3) an electrically insulative seal 206 to ensure that the contacts 104, and thus the terminals in engagement with the contacts 104, are electrically isolated from each other; (4) the previously described connector block 108 associated with the housing 202 to lock the electrical lead within the housing 202; (5) an end cap 216 associated with the housing 202 to serve as an insertion stop for the electrical lead; and (6) an optional electrically insulative covering disposed over the housing 202.

Figure 29:
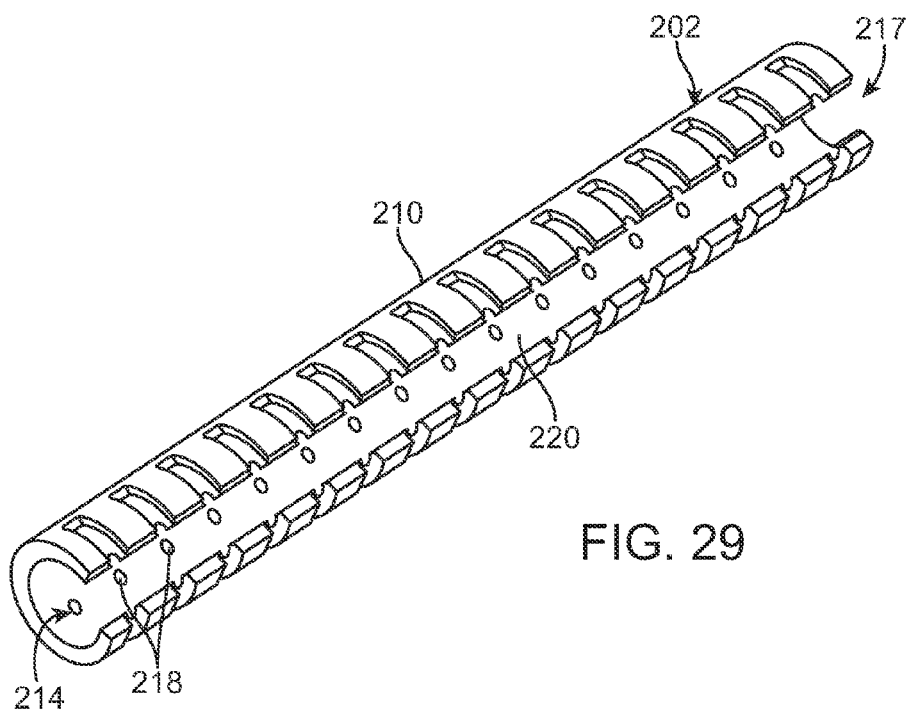
FIG. 29 is a perspective view of an outer housing used in the connector of FIG. 24.
Figure 30:
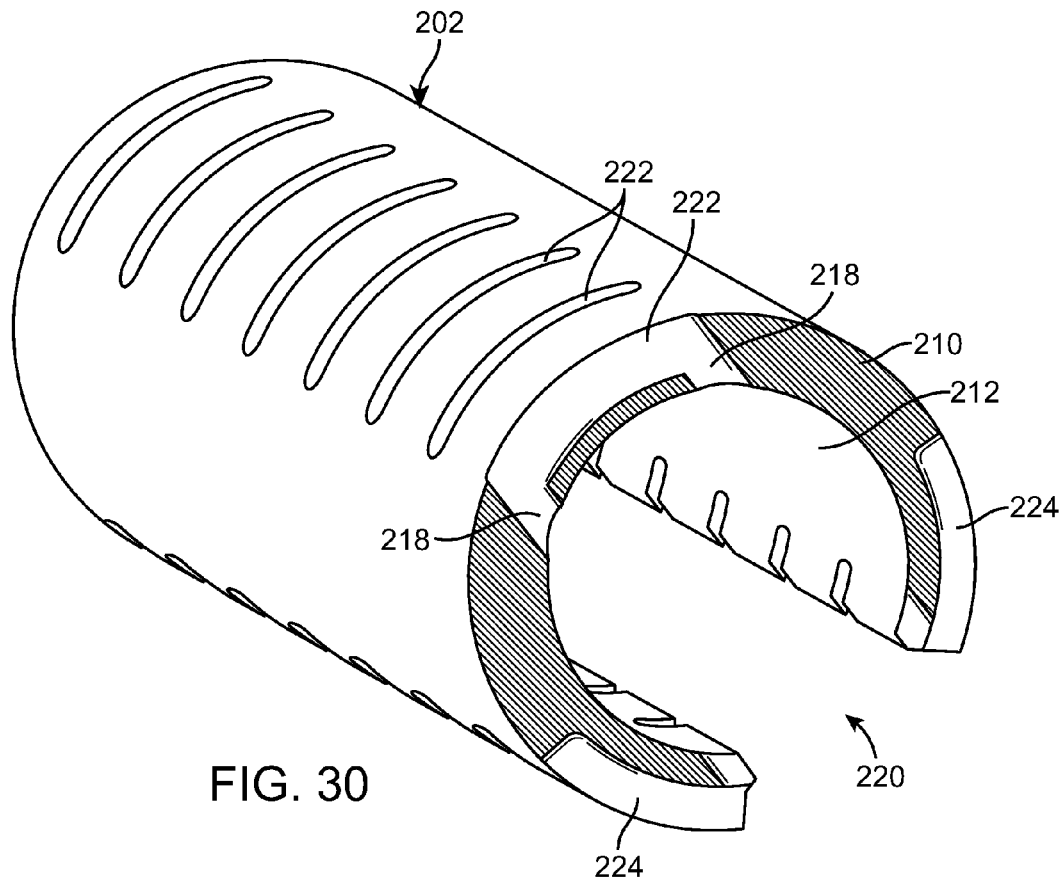
FIG. 30 is a cross-sectional view of the outer housing of FIG. 29.

Referring further to FIGS. 29 and 30, the housing 202 includes an outer wall 210, an interior passage 212 partially surrounded by the outer wall 210, a port 214 into which the proximal end of the electrical lead can be introduced, and an open end 217 opposite the port 214. In the illustrated embodiment, the outer wall 210 takes the form of an open cylinder that includes an axial slot 220 extending the length of the outer wall 210. The outer wall 210 may have the same composition and dimensions as those described above with respect to the outer wall 110.

Like the housing 102, the housing 202 accommodates the contacts 104 using a pattern of apertures and recesses formed within the outer wall 210 using suitable means, such as laser ablation or molding. The housing 202 differs from the housing 102 in that it does not include contact exit apertures. Rather, the axial slot 116 serves as the exit point for the contacts 104.

In particular, the housing 202 includes pairs of contact entry apertures 218 extending through the outer wall 210. The housing 202 further includes a channeled recess 222 formed in the exterior surface of the outer wall 210 adjacent each contact entry aperture pair 218. The contact entry apertures 218 and channel recesses 222 are respectively formed and arranged in the same manner as the contact entry apertures 118 and channel recesses 122 described above. The housing 202 further includes pairs of channeled recesses 224 formed in the exterior surface of the outer wall 210 adjacent the axial slot 220. In particular, the pairs of channeled recesses 224 are axially spaced along the outer wall 210. The recesses 224 of each pair circumferentially extend from the axial slot 220 in opposite directions and are axially aligned with a respective one of the channeled recesses 222.

As shown in FIGS. 25-28, the legs 128 of each contact 104 extend through a respective pair of contact entry apertures 218 into the interior passage 212 of the housing 202, such that the common portion 126 of the respective contact 104 is seated within the recess 222 extending between the contact entry apertures 218, and the middle portions 130 of the legs 128 firmly engage the respective electrical terminal (not shown) therebetween when the proximal end of the electrical lead is introduced into the internal passage 112. Notably, the middle portions 130 of the contact 104 are not shown bent outward (as in FIG. 11), but are shown straight to illustrated an alternative means for engaging the electrical terminal of the electrical lead. The legs 128 of each contact 104 further extend from the interior passage 212 of the housing 202 and through the axial slot 220, such that end portions 132 of the legs 128 are disposed externally to the outer housing 202. The end portions 132 of the legs 128 are curved outward back towards the common portion 126, such that they are seated within the respective recesses 224 extending circumferentially outwardly from the axial slot 220. As described above, the end portions 132 of the legs 128 may be curved using suitable means, such as a crimping tool. Preferably, the depth of the recesses 222, 224 is equal to or greater than diameter of the wire from which the contact 104 is formed, so that no portion of the common portions 126 or legs 128 extends above the external surface of the outer wall 210.

Figure 27:
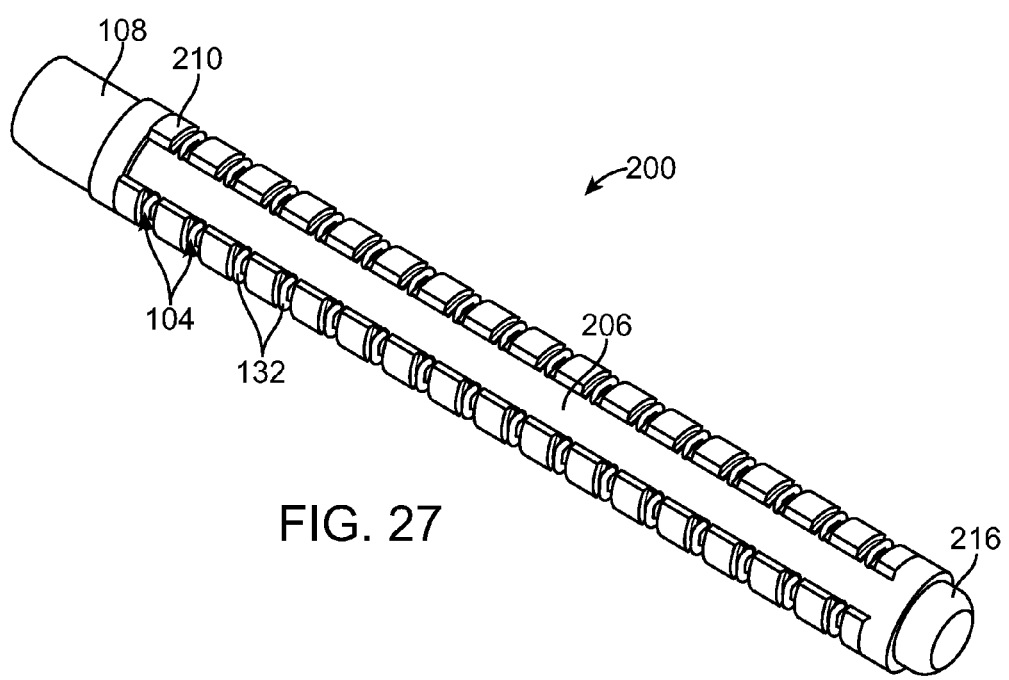
FIG. 27 is still another perspective view of the connector of FIG. 24.
Figure 28:
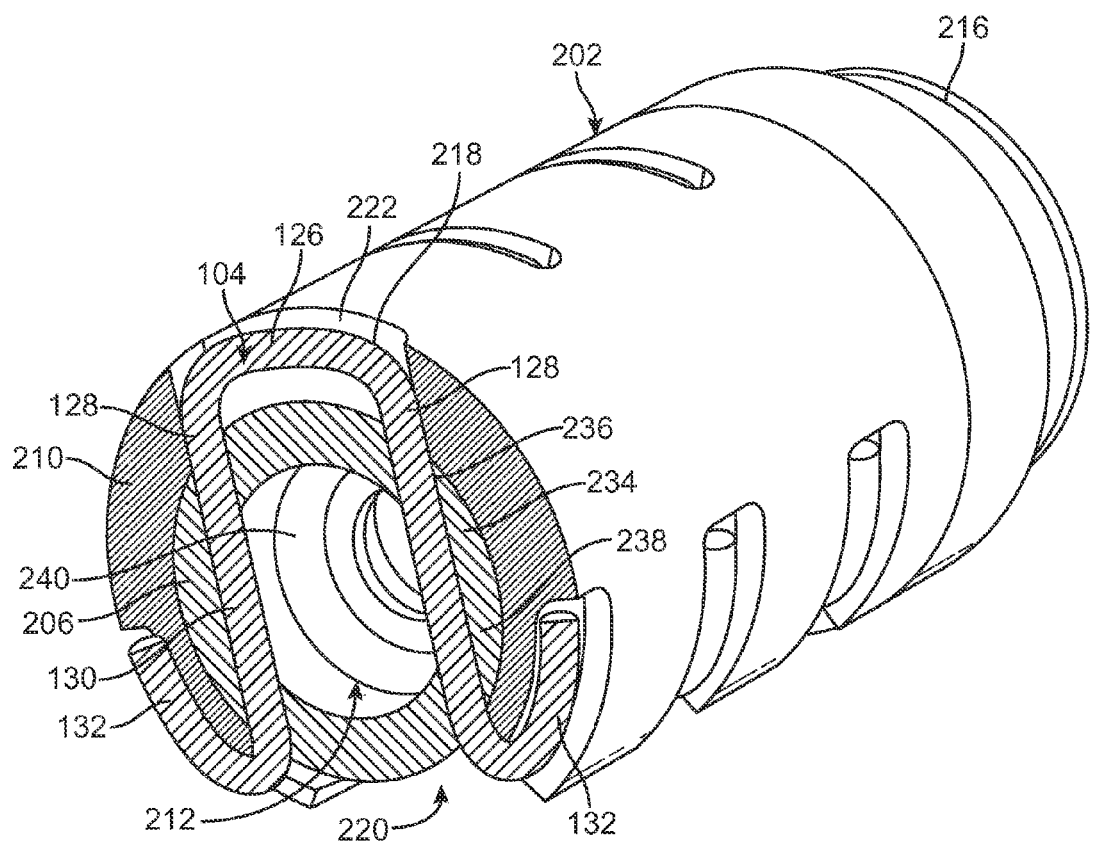
FIG. 28 is a cross-sectional view of the connector of FIG. 24.

Referring to FIGS. 27 and 28, the tubular seal 206 is disposed within the housing 202, and in particular, is interference fit with the interior surface of the housing 202, such that seal 206 surrounds the interior passage 212. The tubular seal 206 may be composed of any electrically insulative and compliant material, such as silicone.

Figure 31:
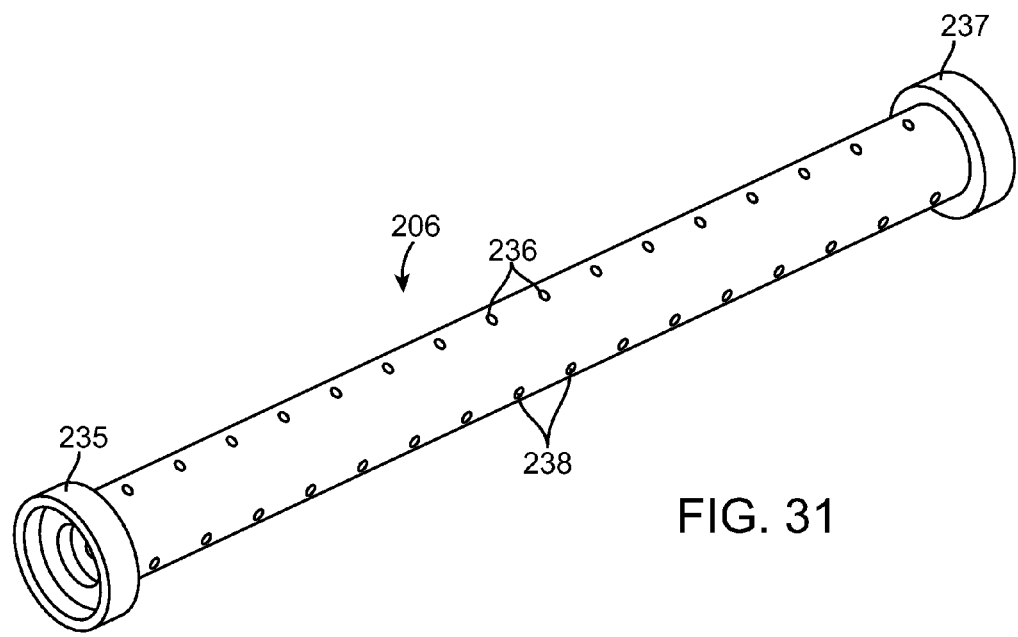
FIG. 31 is a perspective view of a tubular seal used in the connector of FIG. 24.
Figure 32:
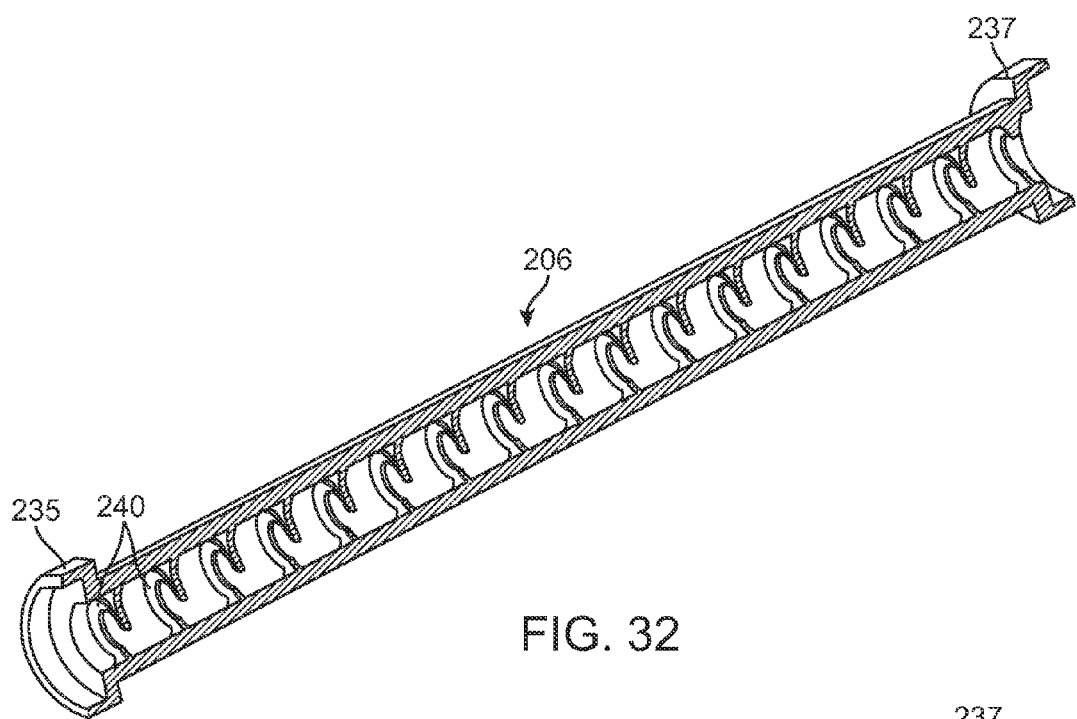
FIG. 32 is a cross-sectional view of the tubular seal of FIG. 31.

Referring further to FIGS. 31 and 32, the tubular seal 206 includes a cylindrical wall 234 having a diameter substantially the same as the inner diameter of the housing 202, such that the tubular seal 206 is snugly fit within the interior passage 212 of the housing 202. The tubular seal 206 includes a first enlarged annular portion 235 disposed on end of the cylindrical wall 234 and a second enlarged annular portion 237 disposed on the other end of the cylindrical wall 234. The length of the tubular seal 206 is such that the first enlarged annular portion 235 extends externally from the port 214 (shown in FIG. 29), and the second enlarged annular portion 237 extends externally from the open end 217 (shown in FIG. 29). The tubular seal 206 includes pairs of contact entry apertures 236, pairs of contact exit apertures 238, and a plurality of inner annular flanges 240 that are arranged and function in the same manner as the contact entry apertures 136, contact exit apertures 138, and inner annular flanges 140 described above.

The annular flange 144 of the connector block 108 (shown in FIG. 20) is mounted within the first enlarged annular portion 235 of the tubular seal 206 using suitable means, such as bonding. The end cap 216 can be composed of the same material as the outer housing 202 and is mounted within the second enlarged annular portion 237 of the tubular seal 206 using suitable means, such as bonding. The electrical conductors (not shown) are respectively connected to the contacts 104 using suitable techniques known in the art, such as welding. The electrically insulative cover is disposed over the housing 202 in such a manner that all exposed surfaces of the contacts 104 are covered, and thereby electrically insulated from each other if the connector 200 comes in contact with tissue or fluids.

Figure 24:
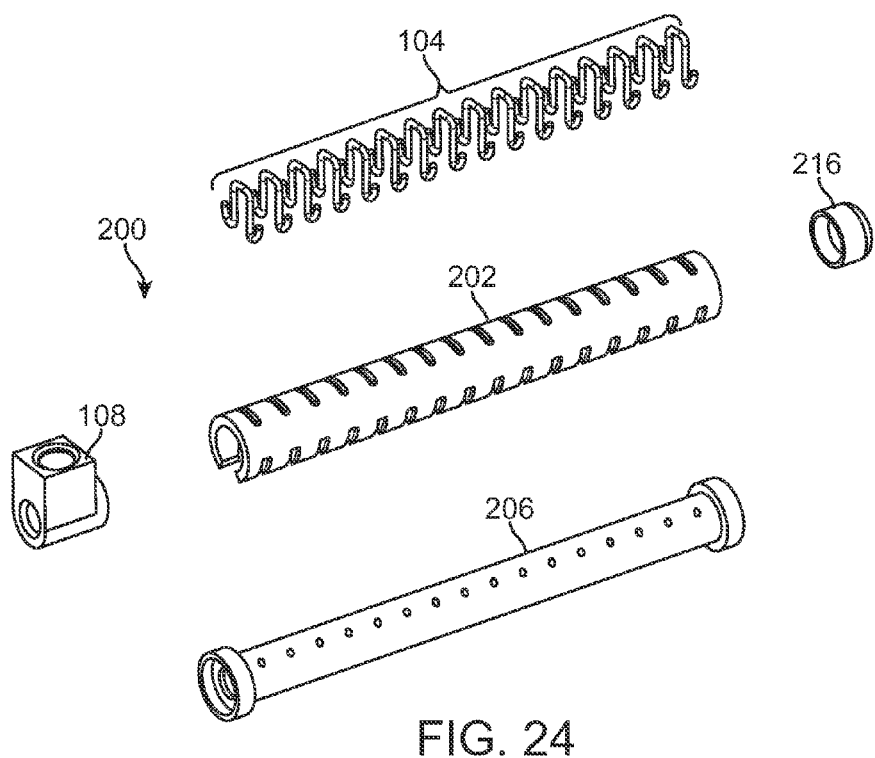
FIG. 24 is an exploded view of another embodiment of a connector constructed in accordance with the present inventions, which can be used in the tissue stimulation system of FIG. 1.
Figure 25:
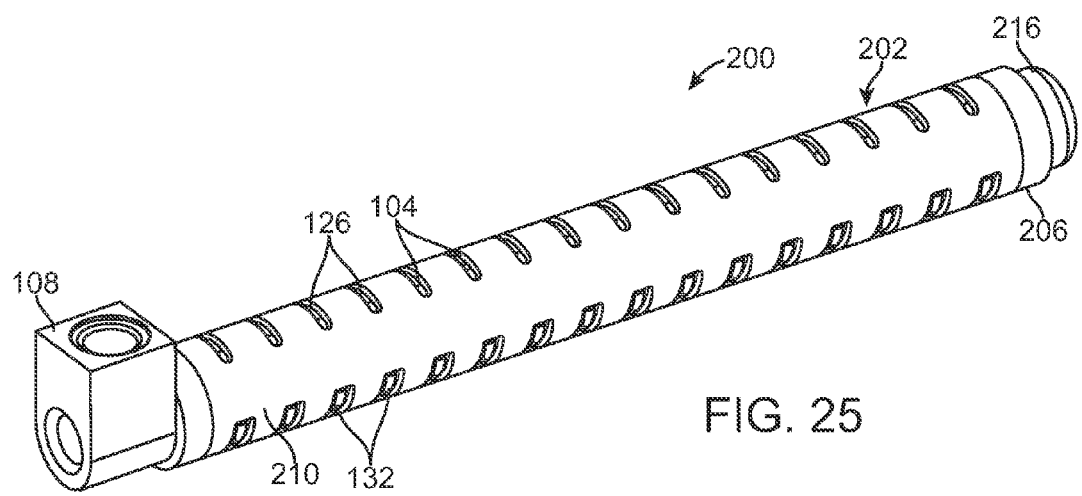
FIG. 25 is one perspective view of the connector of FIG. 24.
Figure 26:
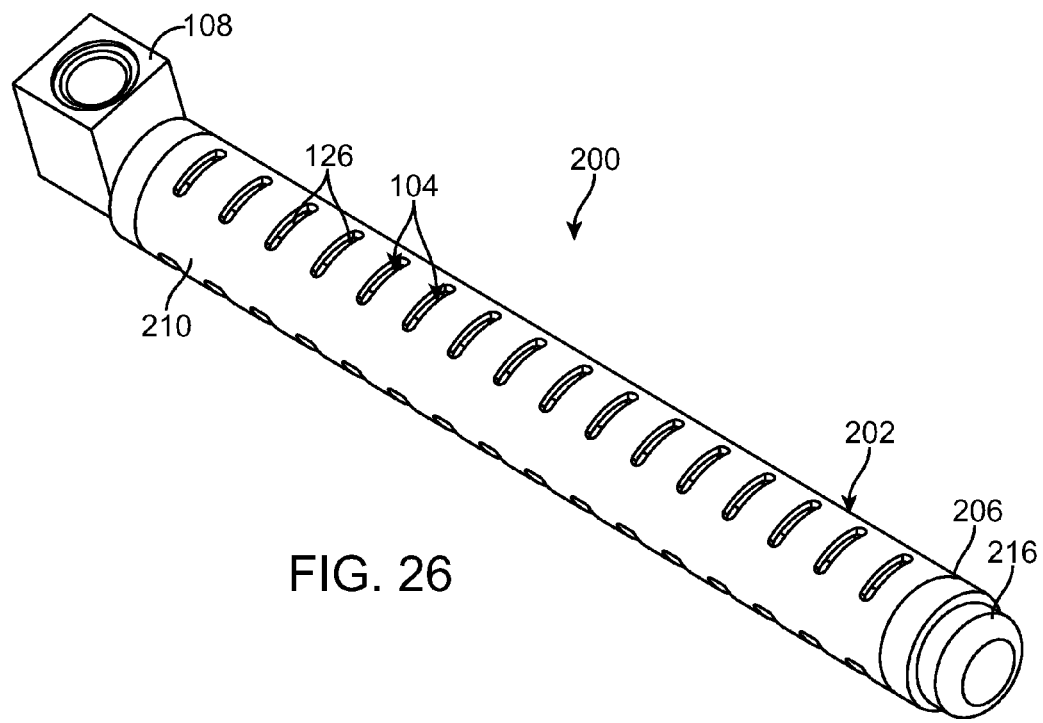
FIG. 26 is another perspective view of the connector of FIG. 24.
Figure 33:
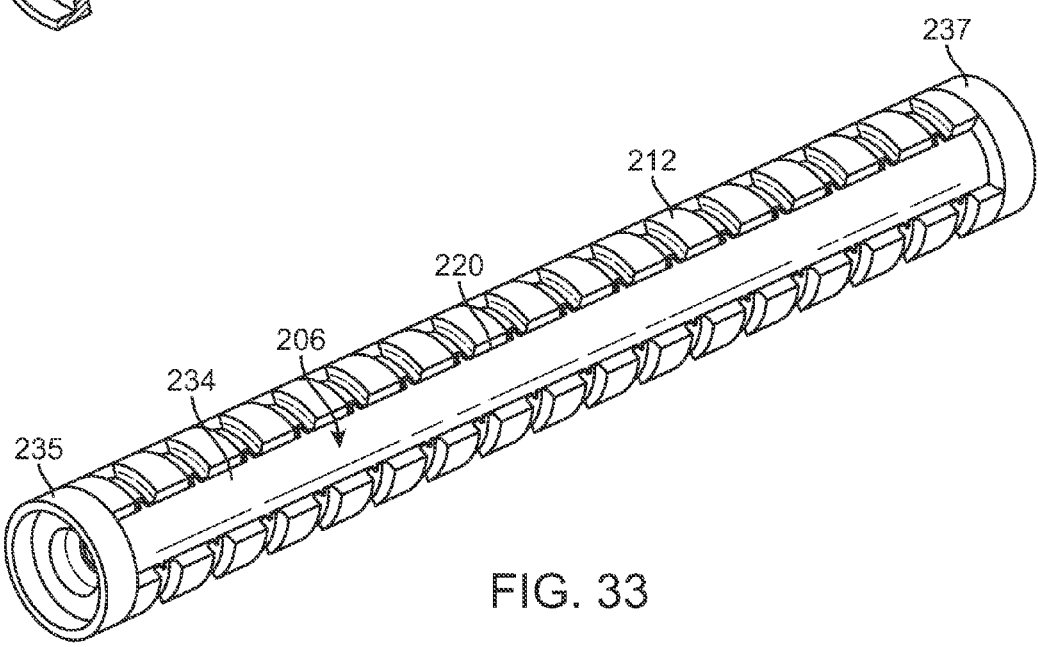
FIG. 33 is a cross-sectional view a subassembly of the connector of FIG. 24, particularly showing the outer housing and tubular seal.
Figure 34:
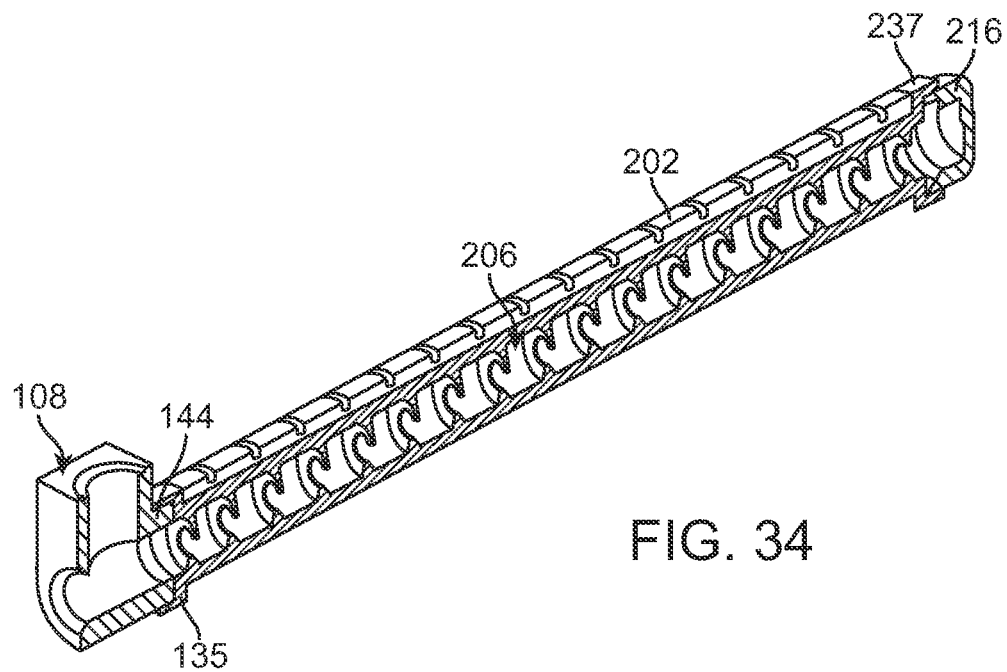
FIG. 34 is a cross-sectional view a subassembly of the connector of FIG. 24, particularly showing the outer housing, tubular seal, connector block, and end cap.
Figure 35:
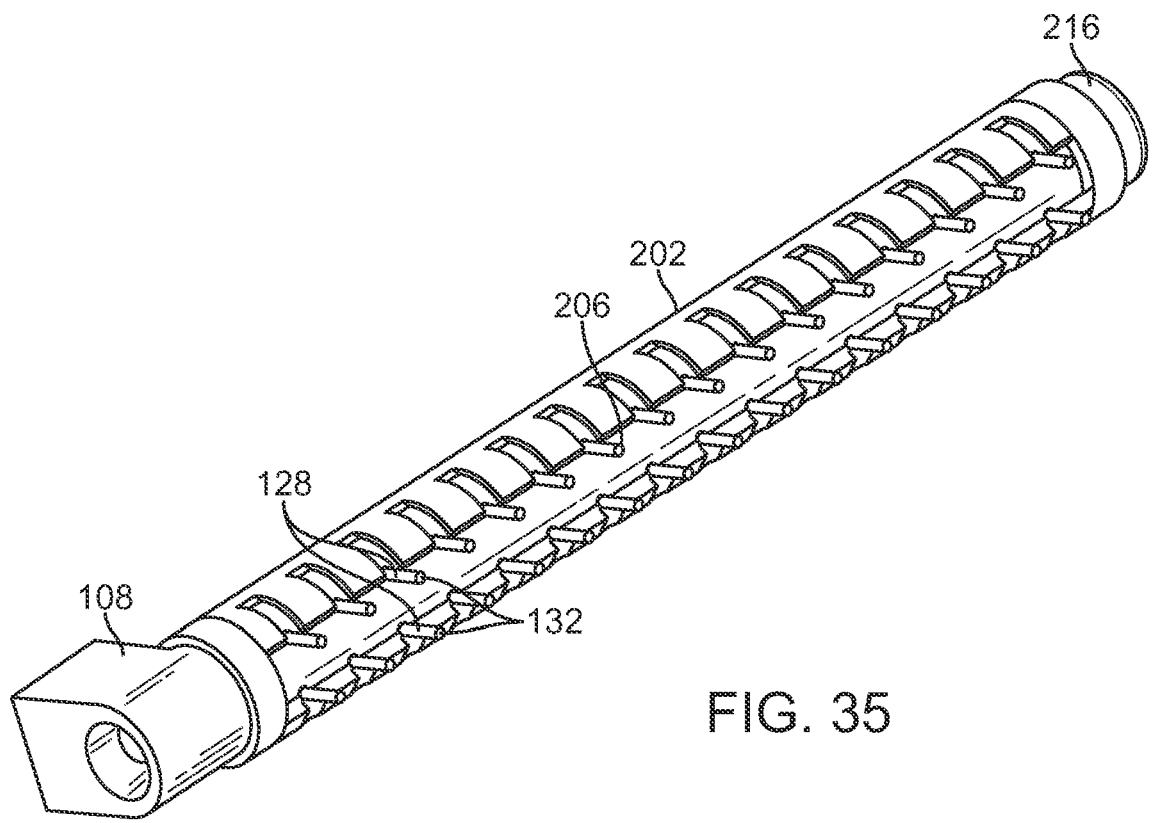
FIG. 35 is a perspective view of a subassembly of the connector of FIG. 24, particularly showing the outer housing, tubular seal, connector block, and uncrimped pins.

Referring to FIGS. 33-35, a method of assembling the components illustrated in FIG. 24 into the connector 200 illustrated in FIGS. 25-27 will now be described. First, as illustrated in FIG. 33, the seal 206 is laterally inserted into the interior passage 212 of the housing 202 via the axial slot 220, such that the cylindrical wall 234 of the seal 206 and housing 212 are interference fit with each other, and the enlarged annular portions 235, 237 of the tubular seal 206 reside outside of the housing 212. As shown in FIG. 34, the annular flange 144 of the connector block 108 is then inserted into the first enlarged annular flange 235 of the seal 206, and the end cap 216 is inserted into the second enlarged annular flange 237 of the seal 206. Next, each contact 104, in its uncrimped form (shown in FIG. 22), is incorporated into the housing 212. In particular, as shown in FIG. 28, the legs 128 of each contact 104 are inserted through the corresponding entry apertures 218 in the housing 202, through the corresponding entry apertures 236 in the seal 206, through the interior passage 212, through the corresponding exit apertures 238 in the seal 106, and out the axial slot 220 in the housing 202. As shown in FIG. 35, the end portions 132 of the respective legs 128 of each contact 104 extend from the housing 202. Next, the end portions 132 of the arms 128 of each contact 104 are crimped away from each other until seated within the recesses 224, as illustrated in FIGS. 27 and 28. Then, the electrical conductors (such as the electrical conductors 58 shown in FIG. 5) would be attached (e.g., via welding) to the contacts 104. Next, the exterior surface of the housing 202 is overmolded with the electrically insulative cover (not shown).

Referring now to FIGS. 36-42, still another embodiment of a connector 300 that can be incorporated into the extension lead 16 and/or neurostimulator 12 (shown in FIGS. 1 and 2) will be described. Like the connector 100, the connector 300 can receive the proximal end of an electrical lead, which can be firmly engaged and locked within the connector 300. Again, the electrical lead may be, e.g., the stimulation lead 14 or the extension lead 16 (shown in FIGS. 1 and 2). In contrast to the connector 100, the connector 300 has a discrete end cap, has a housing that includes oblong or slotted contact entry and exit apertures, allows the spring clip contacts to be snapped into the housing without crimping, and has individual seals.

The connector 300 generally comprises (1) an electrically insulative housing 302 for receiving the proximal end of the electrical lead; (2) a plurality of electrical spring clip contacts 304 (in this case, sixteen contacts) incorporated into the housing 302, such that contacts 304 firmly engage the terminals of an electrical lead that is received into the housing 302; (3) a plurality of electrically insulative seals 306 to ensure that the contacts 104, and thus the terminals in engagement with the contacts 304, are electrically isolated from each other; (4) the previously described connector block 108 associated with the housing 302 to lock the electrical lead within the housing 302; (5) an end cap 316 associated with the housing 302 to serve as an insertion stop for the electrical lead; and (6) an optional electrically insulative covering disposed over the housing 302.

Figure 43:
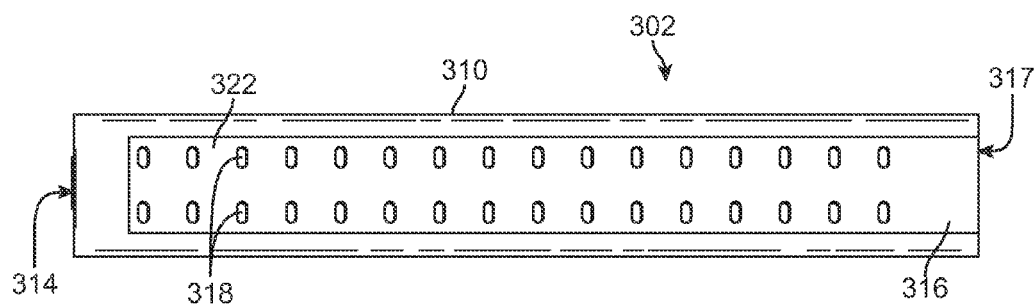
FIG. 43 is a top view of an outer housing used in the connector of FIG. 36.
Figure 44:
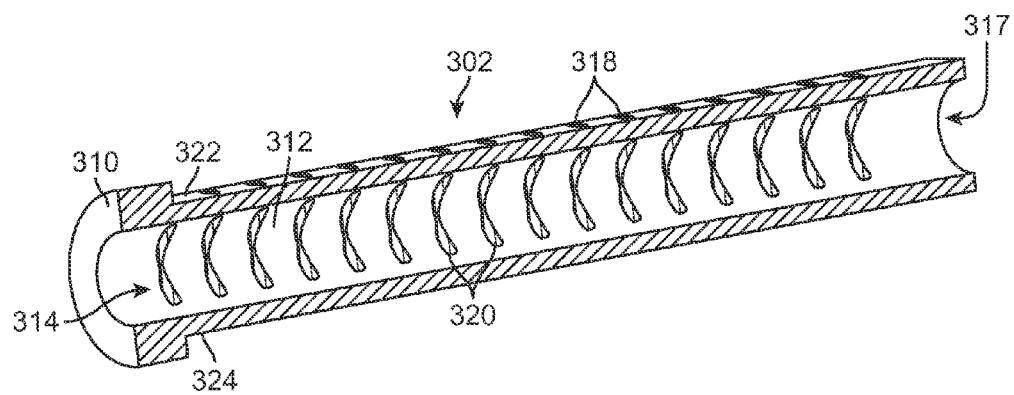
FIG. 44 is a cross-sectional view of the outer housing of FIG. 43, taken along the axis of the housing.
Figure 45:
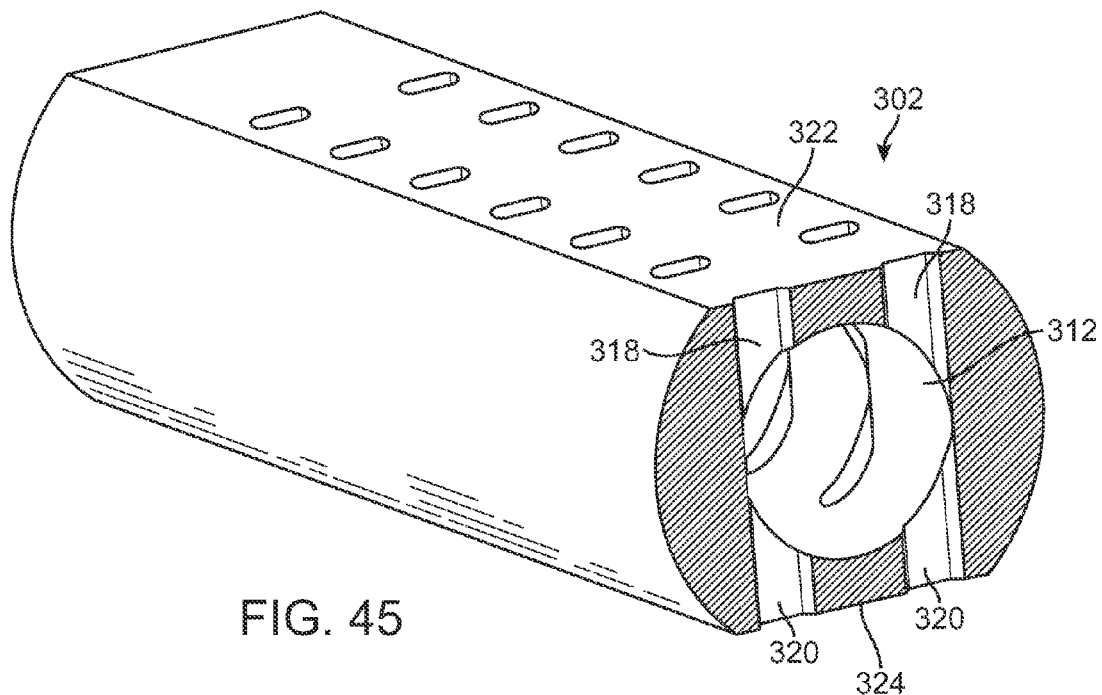
FIG. 45 is a cross-sectional view of the outer housing of FIG. 43, taken transversely to the axis of the housing.

Referring further to FIGS. 43-45, the housing 302 includes an outer wall 310, an interior passage 312 partially surrounded by the outer wall 310, a port 314 into which the proximal end of the electrical lead can be introduced, and an open end 317 opposite the port 314. The outer wall 310 may have the same composition and dimensions as those described above with respect to the outer wall 110.

Like the housing 102, the housing 302 accommodates the contacts 304 using a pattern of apertures formed within the outer wall 310 using suitable means, such as laser ablation or molding. The housing 302 differs from the housing 102 in that it does not include separate recesses for the contacts 204. Rather, a single recess is provided on each side of the outer wall 310 for the contacts 104.

In particular, the housing 302 includes pairs of contact entry apertures 318 and contact exit apertures 320 extending through the outer wall 310. The contact entry apertures 318 and contact exit apertures 320 are arranged in the same manner as the respective contact entry apertures 118 and contact exit apertures 120 described above. The contact entry apertures 318 and contact exit apertures 320 respectively differ from the contact entry apertures 118 and contact exit apertures 120 in that they take the form of elongated holes or slots. The housing 302 further includes a single recess 322 formed in the exterior surface of the outer wall 310 along the contact entry aperture pairs 318, and a single recess 324 formed in the exterior surface of the outer wall 310 along the contact exit aperture pairs 320.

Figure 46:
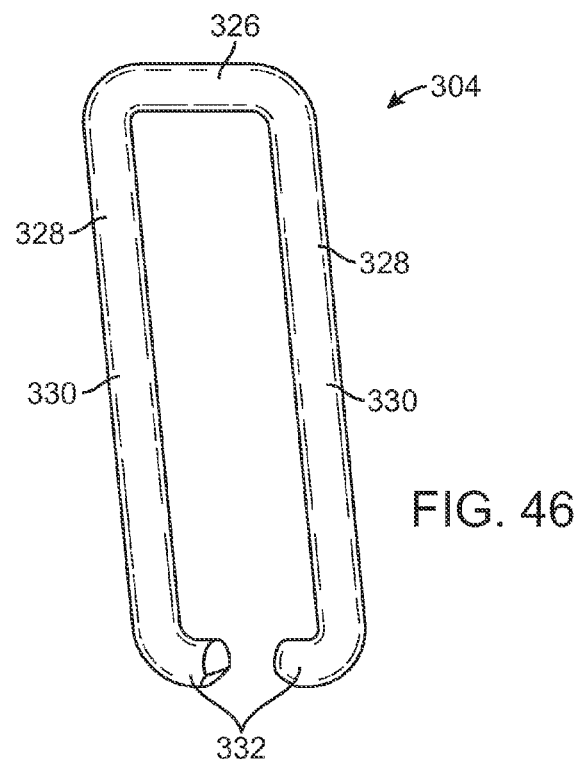
FIG. 46 is a perspective view of an electrical spring clip contact used in the connector of FIG. 36.
Figure 47:
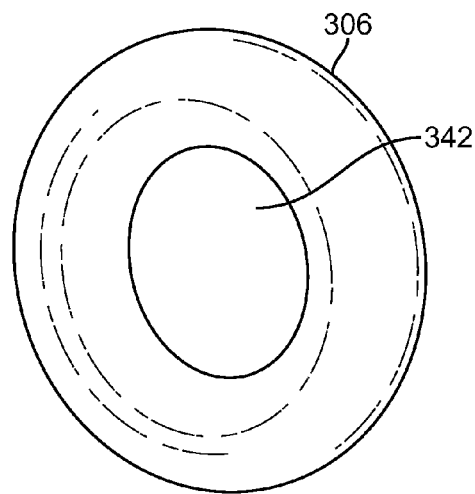
FIG. 47 is a perspective view of a seal used in the connector of FIG. 36.

As shown in FIG. 46, each of the contacts 304 is formed of a cylindrical wire that may be similar to the cylindrical wire from which each of the contacts 104 is formed. Each of the contacts 304 includes a common portion 326 and a pair of legs 328 extending downward from opposite ends of the common portion 326. The length of the common portion 326 equals the distance between the contact entry apertures 318 of each pair, such that the axes of the legs 328 will coincide with the contact entry apertures 318. The legs 328 respectively have middle portions 330 configured for engaging the terminals of the electrical lead. End portions 332 of the legs 328 are bent toward each other at a ninety degree angle. The length of each of the respective legs 328 is greater than the distance between the corresponding apertures 318, 320 through the interior passage 312, such that the legs 328 can completely extend through the interior passage 312.

As shown in FIGS. 37-41, the legs 328 of each contact 304 extend through a respective pair of contact entry apertures 318 into the interior passage 312 of the housing 302, and the middle portions 330 of the legs 328 firmly engage the respective electrical terminal (not shown) therebetween when the proximal end of the electrical lead is introduced into the internal passage 312. The legs 328 of each contact 304 further extend from the interior passage 312 of the housing 302 and through the respective pair of contact exit apertures 320, such that end portions 332 of the legs 328 are disposed externally to the outer housing 302. The end portions 332 of the legs 328 are curved inward, such that they engage the recess 324.

Figure 40:
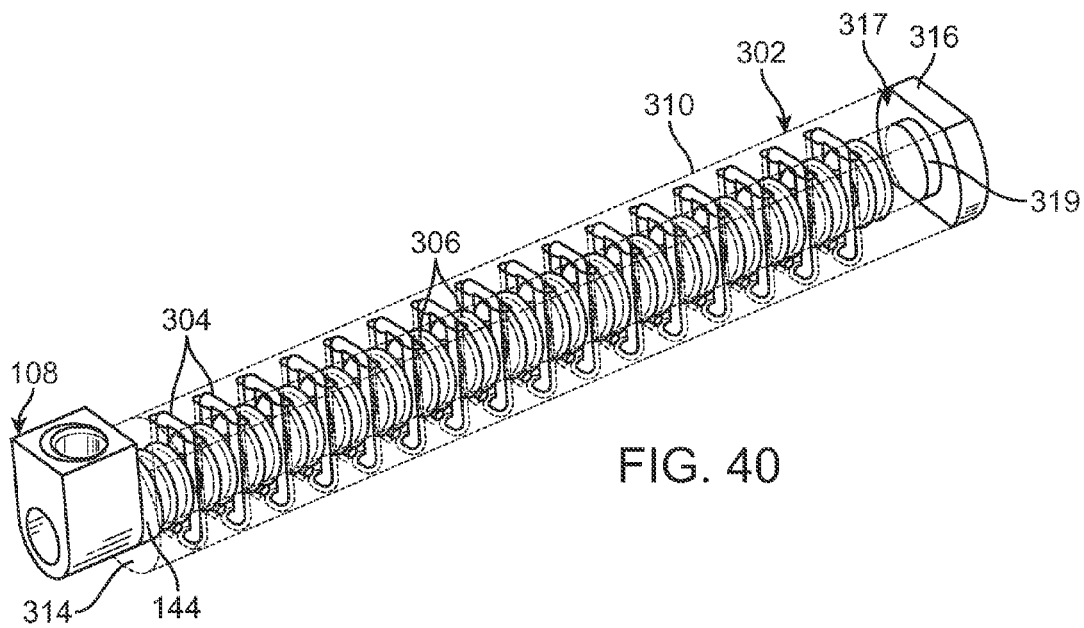
FIG. 40 is a perspective view of the connector of FIG. 36, particularly showing an outer housing of the connector in phantom.
Figure 41:
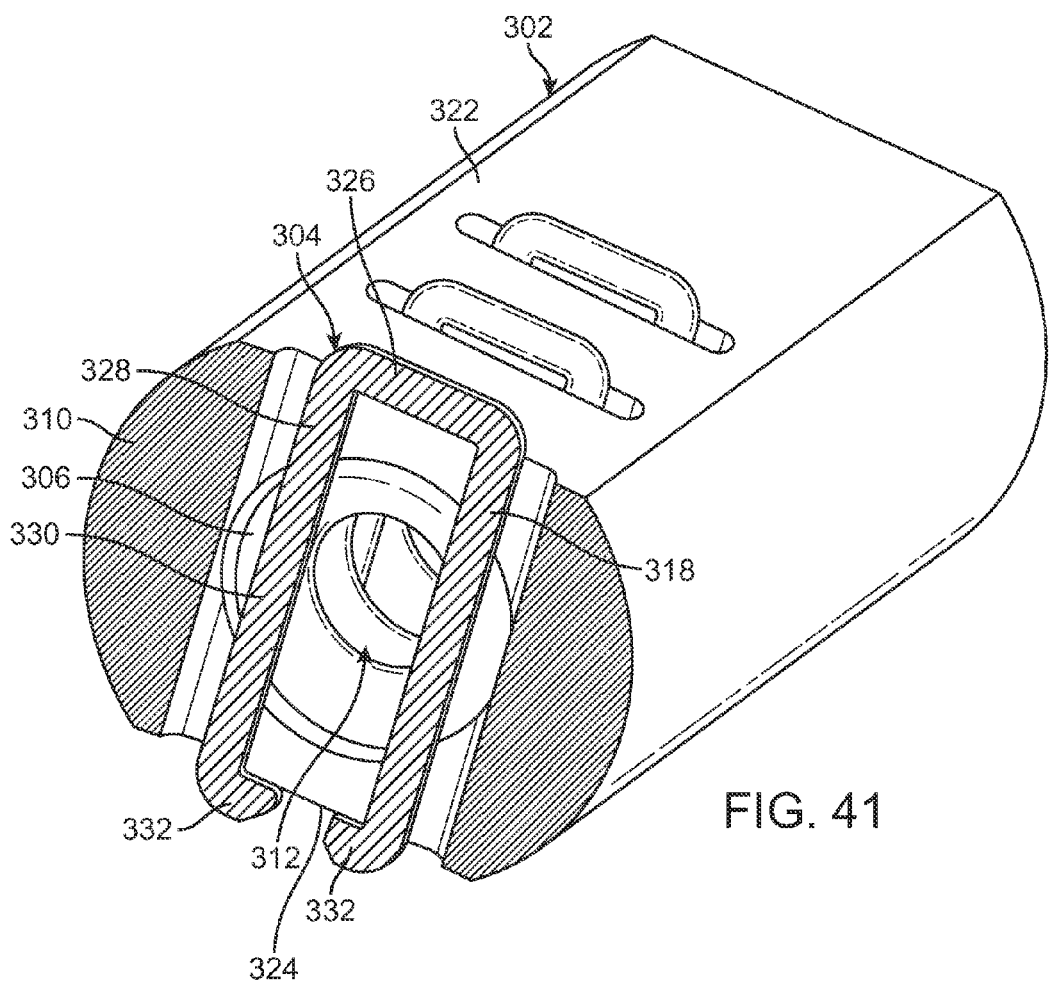
FIG. 41 is a cross-sectional view of the connector of FIG. 36.
Figure 42:
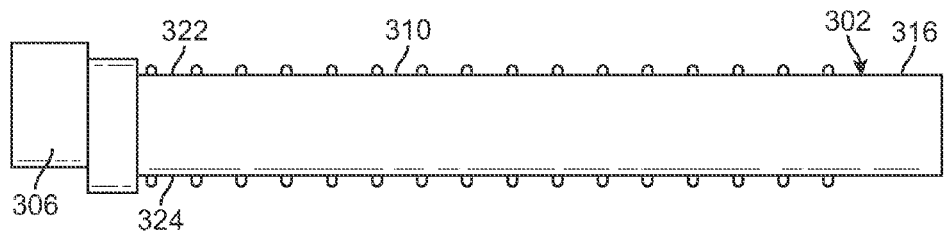
FIG. 42 is a side view of the connector of FIG. 36.

Referring to FIG. 40-42, a plurality of seals 306 in the form of O-rings are disposed within the housing 302, and in particular, are interference fit with the interior surface of the housing 302, such that seals 306 surround the interior passage 312. The tubular seal 306 may be composed of any electrically insulative and compliant material, such as silicone. As there shown, two seals 306 are disposed between each respective pair of contacts 304, such that when the proximal end of the electrical lead is inserted into the interior passage 312 and through center openings 342 in the seals 306, the seals 340 will conform to, and thereby seal, against the outer surface of the electrical lead. As a result, even if an electrolytic fluid enters the interior passage 312 of the outer housing 302, the seals 306 will prevent or, at least minimize, the leakage of electrical current between the contacts 304.

The annular flange 144 of the connector block 108 (shown in FIG. 40) is mounted within the port 314 of the housing 320 using suitable means, such as bonding. The end cap 316 can be composed of the same material as the outer housing 302 includes a boss 319 that is mounted within the opening 317 within the outer housing 302 using suitable means, such as bonding. The electrical conductors (not shown) are respectively connected to the contacts 304 using suitable techniques known in the art, such as welding. The electrically insulative cover is disposed over the housing 302 in such a manner that all exposed surfaces of the contacts 304 are covered, and thereby electrically insulated from each other if the connector 300 comes in contact with tissue or fluids.

Figure 36:
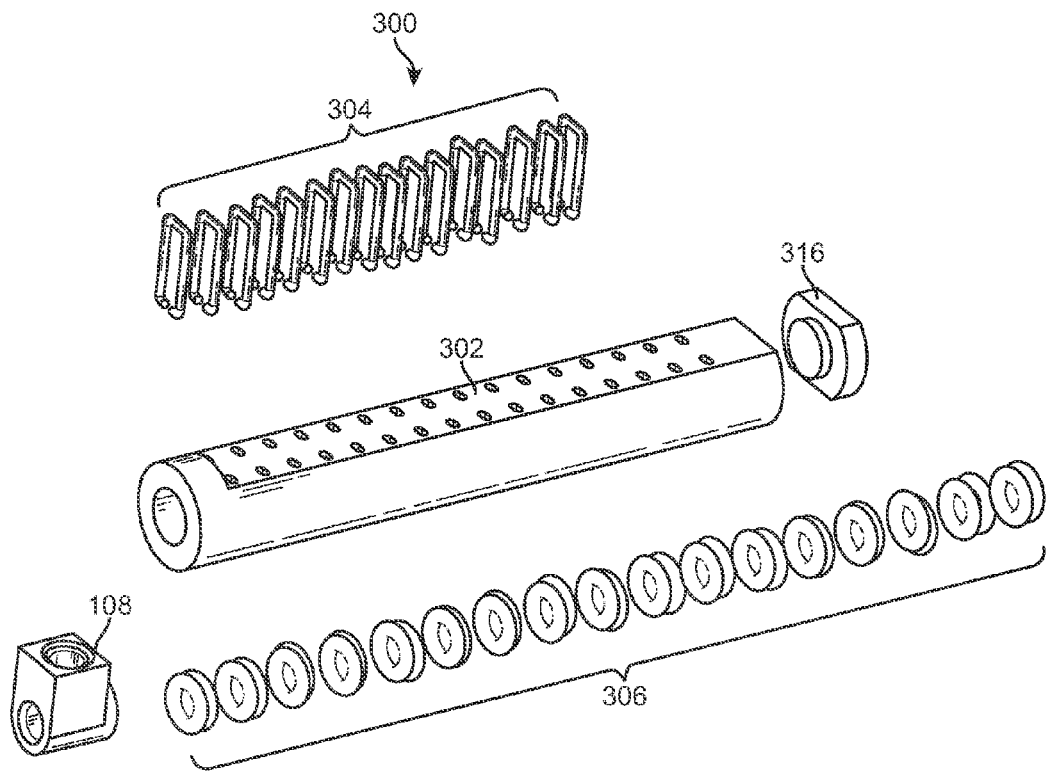
FIG. 36 is an exploded view of still another embodiment of a connector constructed in accordance with the present inventions, which can be used in the tissue stimulation system of FIG. 1.
Figure 37:
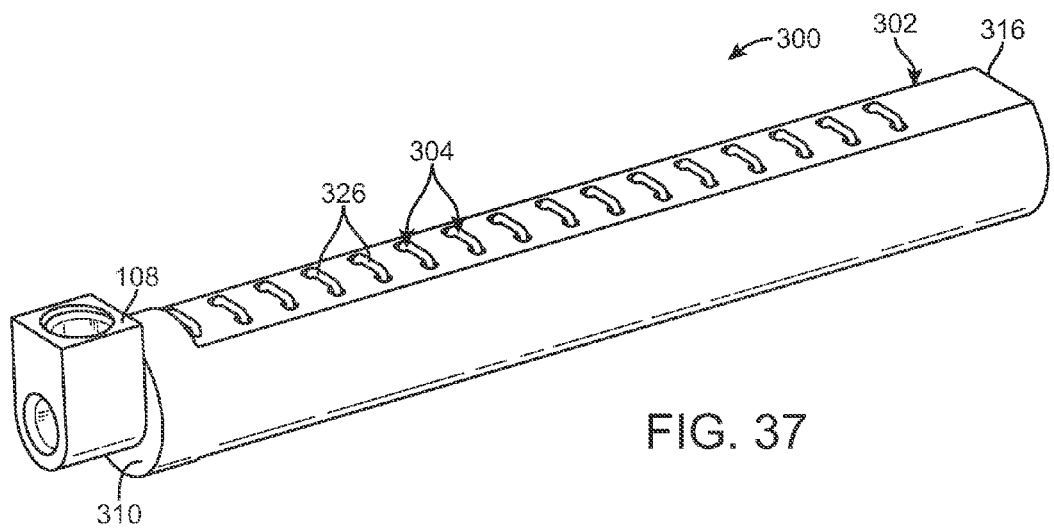
FIG. 37 is one perspective view of the connector of FIG. 36.
Figure 38:
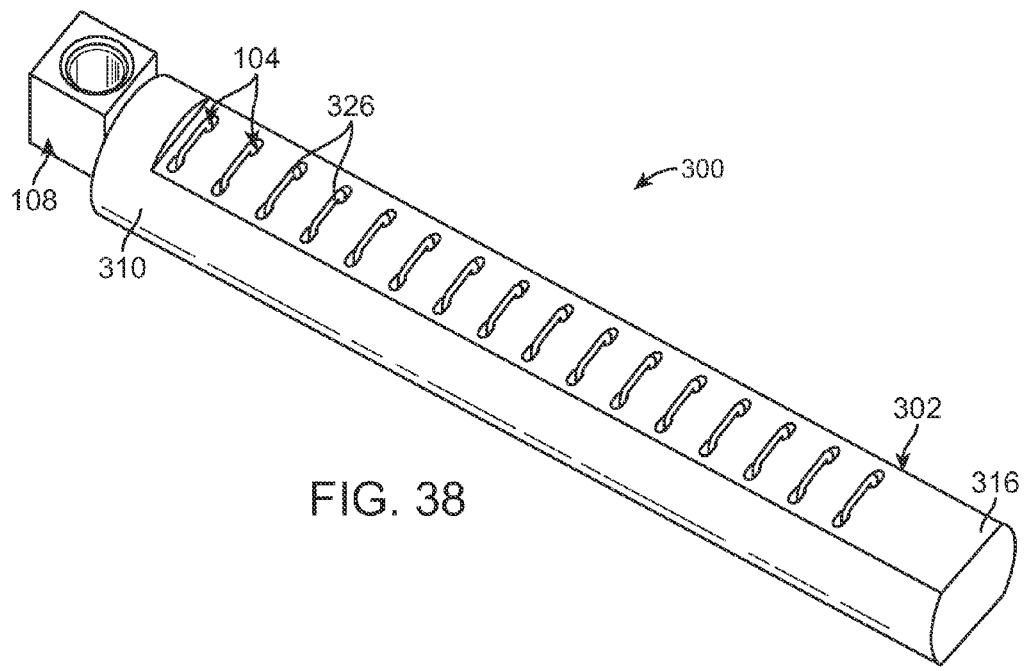
FIG. 38 is another perspective view of the connector of FIG. 36.
Figure 39:
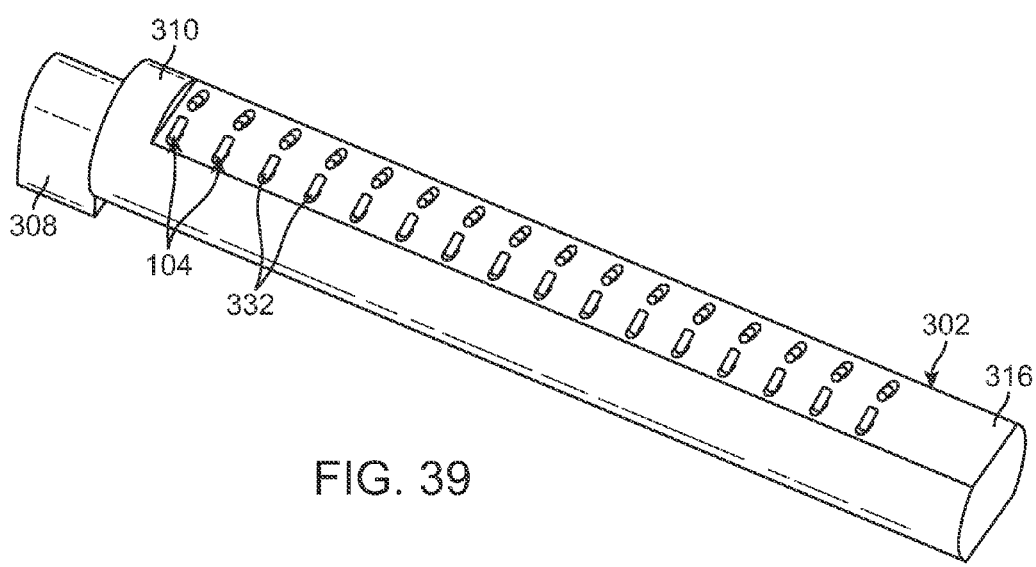
FIG. 39 is still another perspective view of the connector of FIG. 36.

A method of assembling the components illustrated in FIG. 36 into the connector 300 illustrated in FIGS. 37-39 will now be described. First, the seals 306 and contacts 304 are alternatively incorporated into housing 302. That is, two seals 306 are inserted into the interior passage 312 of the housing 302 via the port 314, such that the seals 306 and housing 312 are interference fit with each other, and a contact 304 is mounted to the housing 302. This is repeated until all of the seals 306 and contacts 304 have been incorporated into the housing 302.

Figure 48:
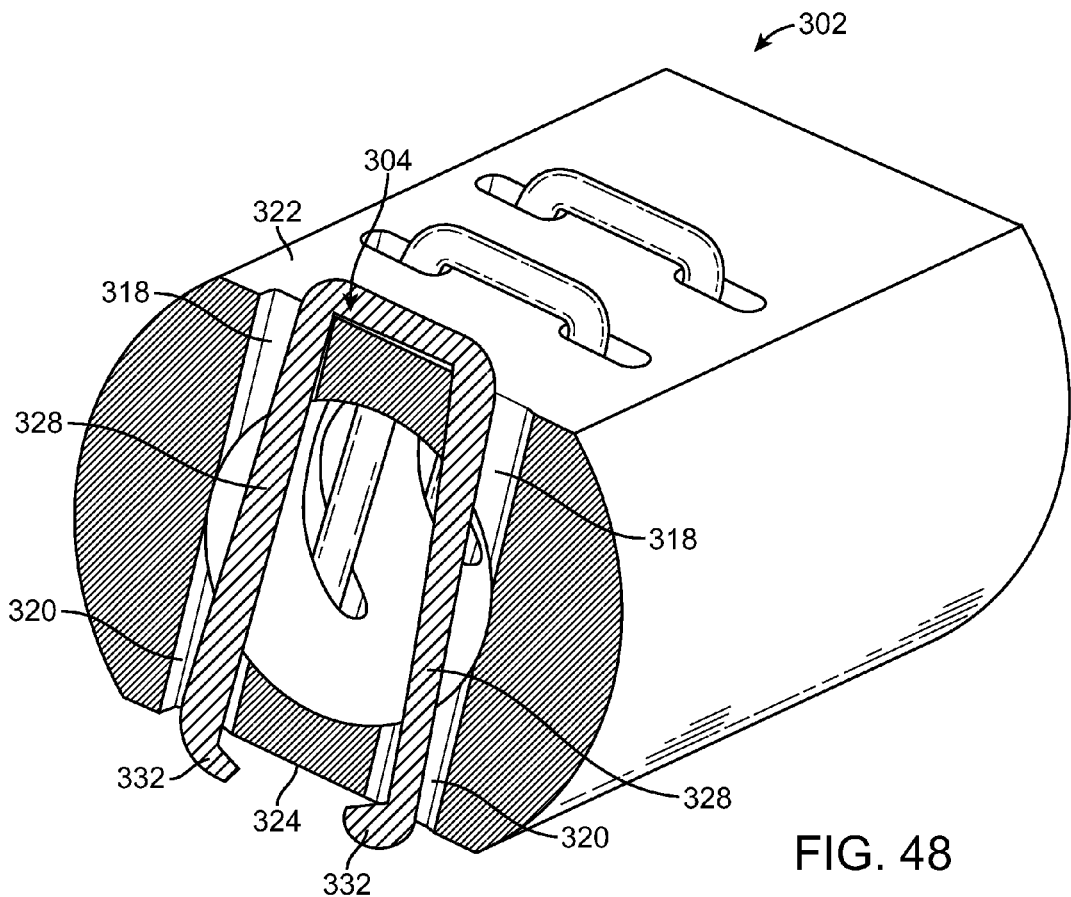
FIG. 48 is a cross-sectional view a subassembly of the connector of FIG. 36, particularly showing the legs of the contact spread outward.

Each of the contacts 304 can be conveniently incorporated into the housing 302 in a snap-fit arrangement. In particular, the legs 328 of each contact 304 are inserted through the corresponding entry apertures 318 in the housing 302, through the interior passage 312, and through the corresponding exit apertures 320 in the housing 302. Notably, the contact entry apertures 318 and contact exit apertures 320 are large enough to allow the curved end portions 332 of the legs 328 to pass through. Also, as shown in FIG. 48, as the end portions 332 of the legs 328 pass through the contact exit apertures 320, the legs 328 are spread apart by the force of the apertures 320 on the end portion 332. When the end portions 332 of the legs 328 completely pass through the respective contact exit apertures 320, the resilient or spring force of the respective contact 304 urges the legs 328 toward each other, thereby placing the end portions 320 in engaging contact with the recess 324, as shown in FIG. 41.

Next, the annular flange 144 of the connector block 108 is inserted into the port 314 of the housing 302, and the boss 319 of the end cap 316 is inserted into the opening 317 in the housing 302. Then, the electrical conductors (such as the electrical conductors 58 shown in FIG. 5) would be attached (e.g., via welding) to the contacts 304. Next, the exterior surface of the housing 302 is overmolded with the electrically insulative cover (not shown).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable connector for receiving an electrical lead body portion that carries an electrical terminal, comprising:
    an electrically insulative housing including an outer wall, an interior cavity surrounded by the outer wall, a port through which the lead body portion can be introduced into the interior cavity, a pair of first apertures disposed through the outer wall on a first side of the housing, at least one opening disposed through the outer wall on a second side of the housing opposite the first side of the housing, and at least one recess within an external surface of the housing adjacent the at least one opening; and
    an electrical spring clip contact mounted to the housing, the contact including a common portion and a pair of legs extending from opposite ends of the common portion, the legs respectively extending through the first apertures into the interior cavity, such that the legs firmly engage the electrical terminal therebetween when the lead body portion is introduced into the interior cavity, the legs further extending from the interior cavity through the at least one opening, wherein ends of the legs are curved, such that they are seated within the at least one recess.

2. The implantable connector of claim 1, wherein the housing wall is cylindrical.

3. The implantable connector of claim 1, wherein the housing is less compliant then the legs.

4. The implantable connector of claim 1, wherein the housing further includes a recess within an external surface of the housing between the first apertures, wherein the common portion is seated within the recess.

5. The implantable connector of claim 4, wherein the recess has a depth, such that the common portion does not extend above the external surface of the housing.

6. The implantable connector of claim 1, wherein the at least one opening comprises a pair of second apertures, and the legs respectively extend from the interior cavity through the second apertures.

7. The implantable connector of claim 1, wherein the at least one opening comprises an axial slot extending along a length of the outer wall, and the legs extend from the interior cavity through the axial slot.

8. The implantable connector of claim 1, wherein the portions of the legs within the interior cavity are radiused outward, such that the radiused portions at least partially wrap around the electrical terminal when the lead body portion is introduced into the interior cavity.

9. The implantable connector of claim 1, further comprising an electrical conductor connected to the contact.

10. The implantable connector of claim 1, further comprising an electrically insulative cover disposed over the housing and common portion.

11. The implantable connector of claim 1, wherein the lead body portion carries a plurality of electrical terminals, and wherein the housing further includes a plurality of pairs of first apertures disposed through the outer wall, the pairs of first apertures axially spaced apart along a length of the housing, the implantable connector further comprising a plurality of electrical spring clip contacts mounted to the housing, each of the contacts including a common portion and a pair of legs extending from opposite ends of the common portion, the legs of each contact respectively extending through a different pair of the first apertures into the interior cavity, such that the legs firmly engage a respective electrical terminal therebetween when the lead body portion is introduced into the interior cavity.

12. The implantable connector of claim 1, wherein each of the at least one recess has a depth, such that the curved legs do not extend above the external surface of the housing.

13. An implantable lead assembly, comprising:
an electrical lead body portion carrying an electrical terminal;
an electrical lead having another lead body portion; and
a connector carried by the other lead body portion, the connector comprising:
an electrically insulative housing including an outer wall, an interior cavity surrounded by the outer wall, a port through which the lead body portion can be introduced into the interior cavity, a pair of first apertures disposed through the outer wall on a first side of the housing, and at least one opening disposed through the outer wall on a second side of the housing opposite the first side of the housing, and at least one recess within an external surface of the housing adjacent the at least one opening; and
an electrical spring clip contact mounted to the housing, the contact including a common portion and a pair of legs extending from opposite ends of the common portion, the legs respectively extending through the first apertures into the interior cavity, such that the legs firmly engage the electrical terminal therebetween when the lead body portion is introduced into the interior cavity, the legs further extending from the interior cavity through the at least one opening, wherein ends of the legs are curved, such that they are seated within the at least one recess.

14. The implantable lead assembly of claim 13, wherein each of the at least one recess has a depth, such that the curved legs do not extend above the external surface of the housing.

15. A method of manufacturing a connector, comprising:
providing an electrically insulative housing including an outer wall, an interior cavity surrounded by the outer wall, a port through which the lead body portion can be introduced into the interior cavity, a pair of first apertures disposed through the outer wall on a first side of the housing, at least one opening disposed through the outer wall on a second side of the housing opposite the first side of the housing, and at least one recess within an external surface of the housing adjacent the at least one opening;
providing an electrical spring clip contact mounted to the housing, the contact including a common portion and a pair of legs extending from opposite ends of the common portion;
respectively inserting the legs through the first apertures into the interior cavity, such that the legs firmly engage the electrical terminal therebetween when the lead body portion is introduced into the interior cavity;
inserting the legs from the interior cavity through the at least one opening: and
bending ends of the legs away from each other until the ends of the legs are seated within the at least one recess.

16. The method of claim 15, further comprising crimping each arm to form a radiused portion, such that the radiused portions are disposed within the interior cavity when the legs are respectively inserted through the first apertures.

17. The method of claim 15, further comprising applying an electrically insulative cover to an exterior surface of the housing.

18. The method of claim 15, wherein each of the at least one recess has a depth, such that the bent legs do not extend above the external surface of the housing.

* * * * *